(12) United States Patent
Hiraoka

(10) Patent No.: US 9,084,541 B2
(45) Date of Patent: Jul. 21, 2015

(54) X-RAY COMPUTED TOMOGRAPHY APPARATUS

(71) Applicant: Manabu Hiraoka, Nasushiobara (JP)

(72) Inventor: Manabu Hiraoka, Nasushiobara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 169 days.

(21) Appl. No.: 13/654,742

(22) Filed: Oct. 18, 2012

(65) Prior Publication Data

US 2013/0039457 A1     Feb. 14, 2013

Related U.S. Application Data

(63) Continuation of application No. PCT/JP2012/067967, filed on Jul. 13, 2012.

(30) Foreign Application Priority Data

Jul. 13, 2011   (JP) ................................ 2011-154857

(51) Int. Cl.
*A61B 6/03* (2006.01)
*A61B 6/00* (2006.01)

(52) U.S. Cl.
CPC .. *A61B 6/03* (2013.01); *A61B 6/541* (2013.01)

(58) Field of Classification Search
CPC ............................... A61B 6/032; A61B 6/541
USPC ...................................................... 378/4–20
See application file for complete search history.

(56) References Cited

U.S. PATENT DOCUMENTS

| 7,756,241 | B2 | 7/2010 | Mukumoto et al. |
| 2003/0161435 | A1 | 8/2003 | Ozaki |
| 2005/0089133 | A1 | 4/2005 | Tsuyuki |
| 2007/0053483 | A1 | 3/2007 | Nagata et al. |
| 2007/0189436 | A1 | 8/2007 | Goto et al. |
| 2007/0237286 | A1 | 10/2007 | Imai |
| 2009/0060120 | A1* | 3/2009 | Mukumoto et al. ............... 378/8 |

FOREIGN PATENT DOCUMENTS

| CN | 1440725 A | 9/2003 |
| CN | 1589742 A | 3/2005 |

(Continued)

OTHER PUBLICATIONS

Combined Chinese Office Action and Search Report issued Jul. 11, 2014 in Patent Application No. 201280000941.4 (with English language translation).

(Continued)

*Primary Examiner* — Hoon Song
(74) *Attorney, Agent, or Firm* — Oblon, McClelland, Maier & Neustadt, L.L.P.

(57) ABSTRACT

According to one embodiment, an input unit repeatedly inputs a trigger signal originating from a specific cardiac phase from an electrocardiograph. An RR period determination unit determines whether the period between the input time point of the latest trigger signal, of repeatedly input trigger signals, and the input time point of an immediately previously input trigger signal is equal to or more than the preset first threshold, for each input of the latest trigger signal. A scan control unit terminates the generation of X-rays, if it is determined that the period is equal to or more than the first threshold.

11 Claims, 15 Drawing Sheets

(56) References Cited

FOREIGN PATENT DOCUMENTS

| | | |
|---|---|---|
| CN | 1927123 A | 3/2007 |
| CN | 1968654 A | 5/2007 |
| CN | 101375799 A | 3/2009 |
| JP | 2000-262513 | 9/2000 |
| JP | 2003-319934 | 11/2003 |
| JP | 2005-66042 | 3/2005 |
| JP | 2005-287949 | 10/2005 |
| JP | 2007-117719 | 5/2007 |
| JP | 2007-275314 | 10/2007 |
| JP | 2008-284017 | 11/2008 |
| JP | 2009-72572 | 4/2009 |
| JP | 2009-148482 | 7/2009 |
| JP | 2009-254893 | 11/2009 |
| JP | 2010-075558 A | 4/2010 |
| JP | 2011-000158 | 1/2011 |
| WO | WO 2005/122901 A1 | 12/2005 |

OTHER PUBLICATIONS

International Search Report issued Oct. 16, 2012 in Application No. PCT/JP2012/067967.

* cited by examiner

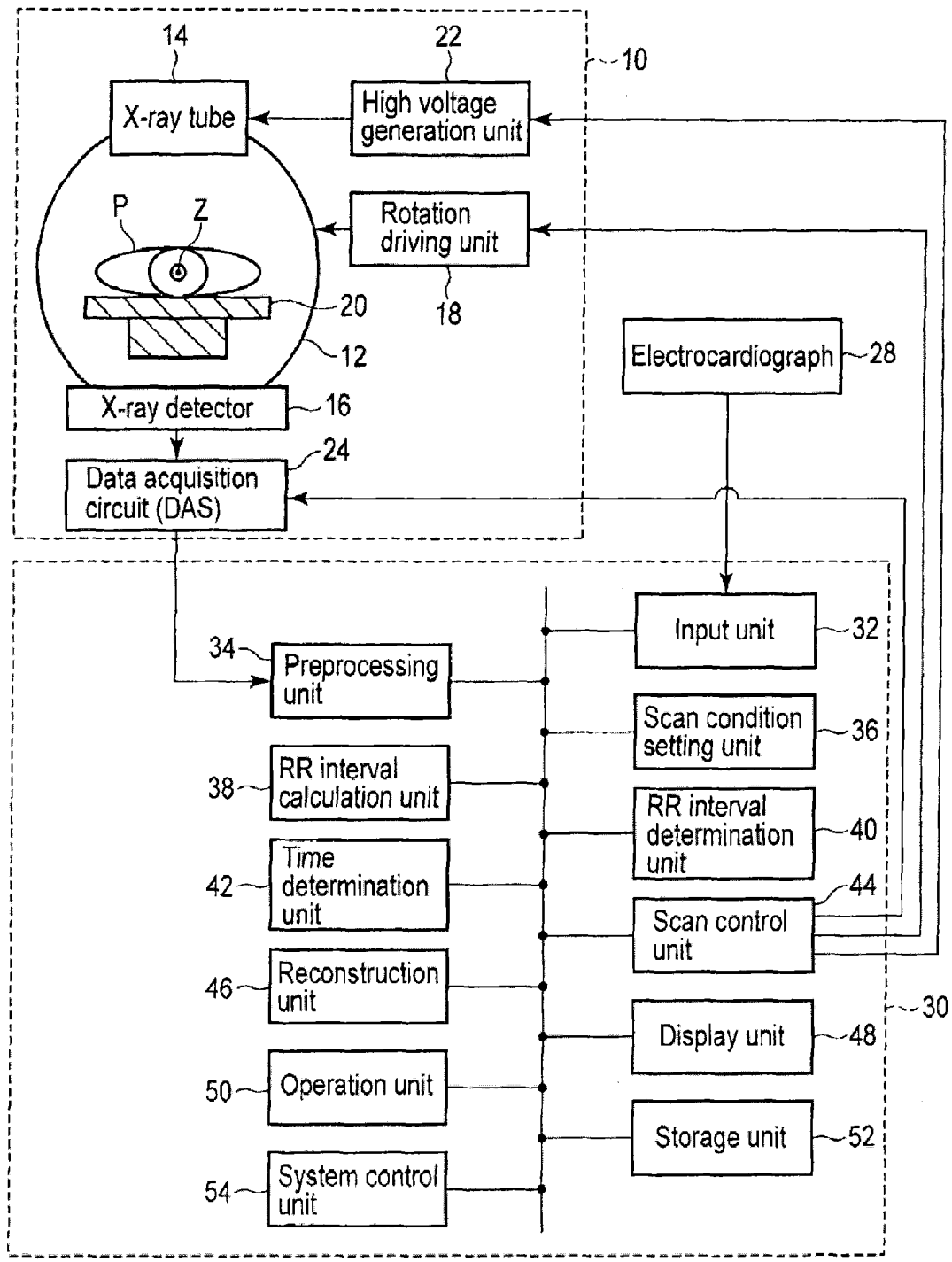
F I G. 1

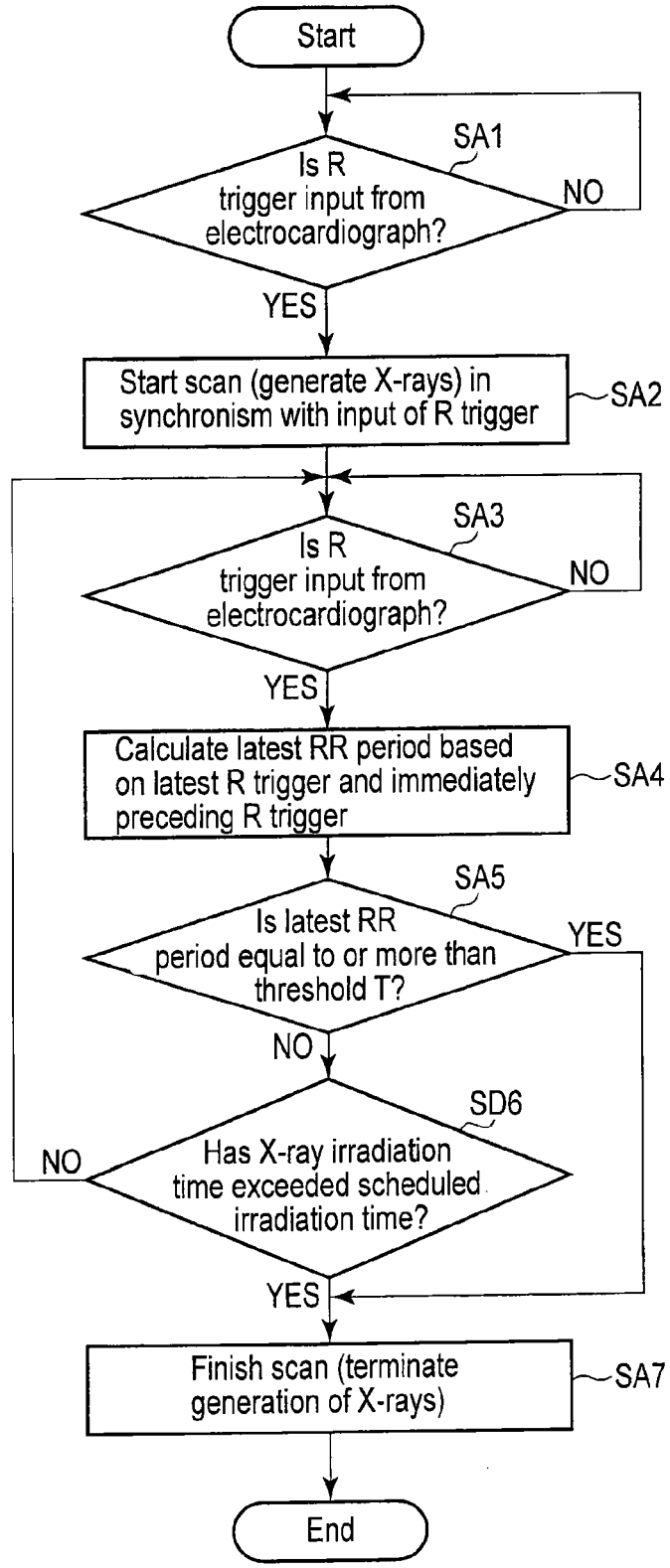
F I G. 6

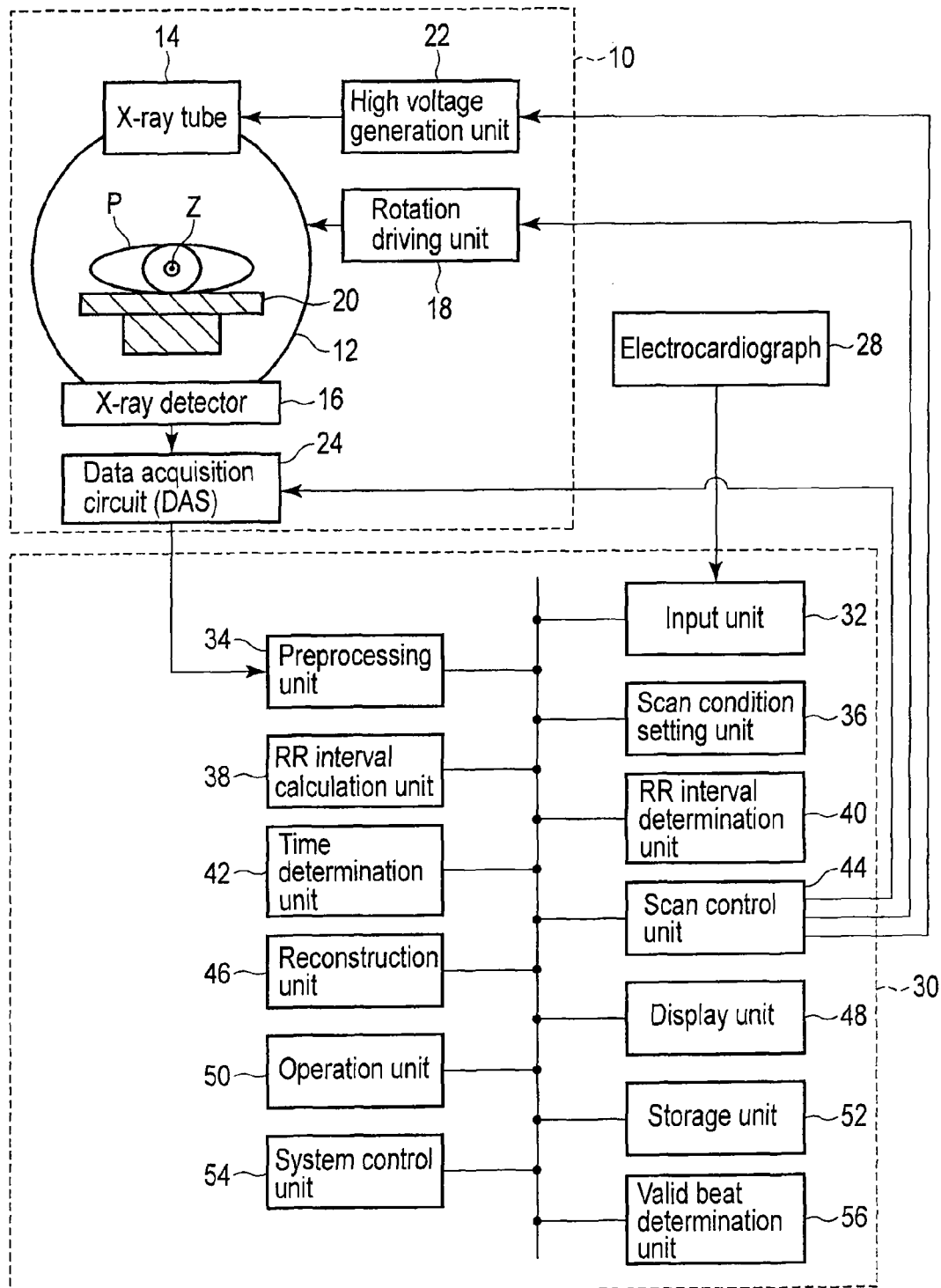
F I G. 7

| Irradiation mode | Valid beat condition |
|---|---|
| Continuous irradiation | None (satisfied unconditionally) |
| Tube current modulation irradiation | Have X-rays been generated with high tube current at reconstruction phase? |
| ON/OFF irradiation (intermittent irradiation) | Have X-rays been generated at reconstruction phase? |

F I G. 9

| Set beat count m = 3 | | Imaging beat count = 2 | | |
|---|---|---|---|---|
| m | BN | 1st beat | 2nd beats | 3rd beats |
| 1 | 0 | × | × | × |
| 2 | 2 | ○ | ○ | – |
| 3 | 2 | ○ | ○ | – |

○ : Valid beat
× : Invalid beat

| Scan condition / Target valid beat count | 1 | 2 | 3 | ... |
|---|---|---|---|---|
| 1 | T1= 1100ms | T1= 1050ms | T1= 1000ms | |
| 2 | T2= 900ms | T2= 850ms | T2= 800ms | |
| 3 | T3= 800ms | T3= 750ms | T3= 700ms | |
| ⋮ | | | | |

FIG. 16

X-RAY COMPUTED TOMOGRAPHY APPARATUS

CROSS REFERENCE TO RELATED APPLICATIONS

This application is a Continuation Application of PCT Application No. PCT/JP2012/067967, filed Jul. 13, 2012 and based upon and claiming the benefit of priority from Japanese Patent Application No. 2011-154857, filed Jul. 13, 2011, the entire contents of all of which are incorporated herein by reference.

FIELD

Embodiments described herein relate generally to an X-ray computed tomography apparatus.

BACKGROUND

As one of the scan schemes in an X-ray computed tomography apparatus, there is available a scheme of scanning the heart in synchronism with signals from an electrocardiograph (i.e., ECG gated scanning). In ECG gated scanning, to obtain optimal time resolution, scanning is performed for only a period corresponding to a preset beat count. A beat count is decided in accordance with the heart rate (beat count per unit time) or the like of a subject which is measured before a scan. In some case, the heart rate becomes lower than that before a scan, and projection data which can be reconstructed is acquired in one pulsation (beat). However, a scan does not finish unless the scan time elapses. That is, unnecessary X-rays which are not used for reconstruction have been applied. Assume that a short scheduled scan time is set. In this case, when the heart rate becomes higher than that at the time of scanning, the scan finishes before the acquisition of projection data necessary and sufficient for reconstruction. This makes it necessary to set a relatively long scan time.

It is an object to provide an X-ray computed tomography apparatus which can improve the scan efficiency concerning ECG gated scanning.

BRIEF DESCRIPTION OF THE DRAWINGS

FIG. 1 is a block diagram showing the arrangement of an X-ray computed tomography apparatus according to the first embodiment.

FIG. 6 is a flowchart showing a typical procedure for ECG gated scanning performed by a system control unit according to the second embodiment.

FIG. 7 is a block diagram showing the arrangement of an X-ray computed tomography apparatus according to the third embodiment.

FIG. 9 is a view showing the valid beat conditions determined by a valid beat determination unit in FIG. 7.

FIG. 16 is a view showing an example of a table which outputs thresholds upon receiving target valid beat counts and scan conditions and is used by a scan condition setting unit in FIG. 12.

DETAILED DESCRIPTION

Figure 2:
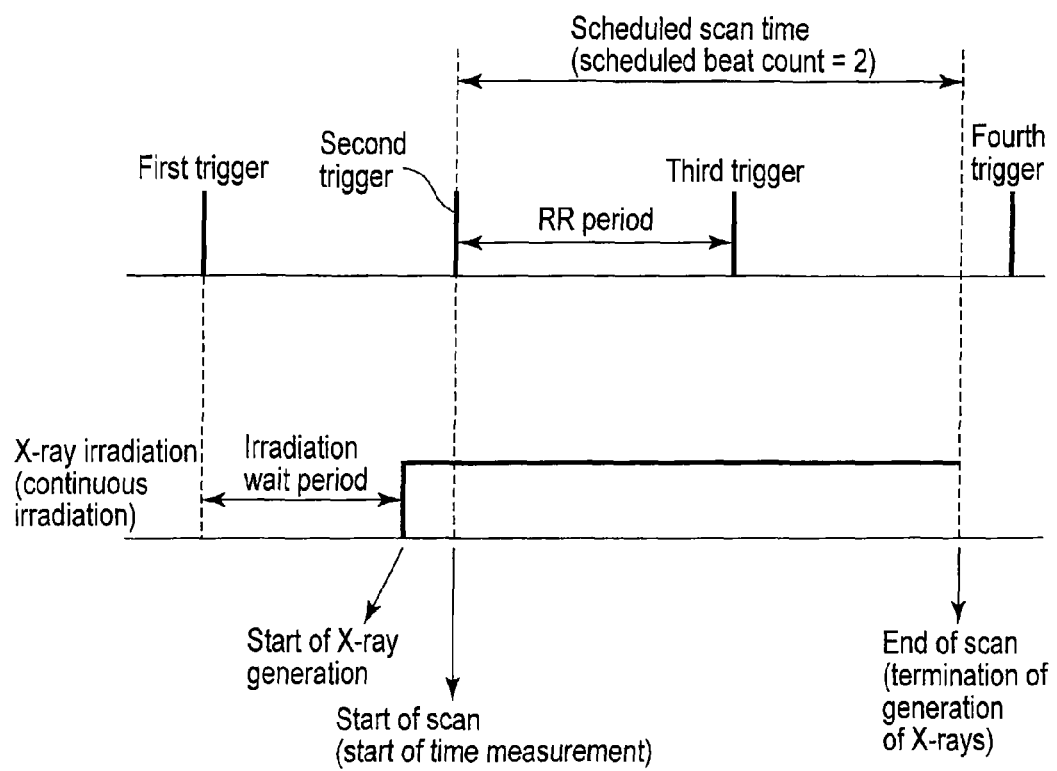
FIG. 2 is a chart showing a standard sequence for ECG gated scanning.

In general, according to one embodiment, an X-ray computed tomography apparatus includes an X-ray tube, an X-ray detector, a support mechanism, an input unit, an RR period determination unit, and a control unit. The X-ray tube generates X-rays. The X-ray detector detects X-rays generated from the X-ray tube and transmitted through a subject. The support mechanism rotatably supports the X-ray tube and the X-ray detector. The input unit repeatedly inputs, from an electrocardiograph, a trigger signal originating from a specific cardiac phase in a cardiac cycle of the heart of the subject. The RR period determination unit determines whether a period between an input time point of a latest trigger signal, of the repeatedly input trigger signals, and an input time point of a trigger signal immediately before the latest trigger signal is not less than a preset first threshold, for each input of the latest trigger signal. The control unit terminates generation of X-rays from the X-ray tube, if it is determined that the period is not less than the first threshold.

An X-ray computed tomography apparatus (to be referred to as an X-ray CT apparatus hereinafter) according to an embodiment will be described below with reference to the accompanying drawing.

X-ray CT apparatuses include various types of apparatuses, e.g., a rotate/rotate-type apparatus in which an X-ray tube and an X-ray detector rotate together around a subject, and a stationary/rotate-type apparatus in which many detection elements are arrayed in the form of a ring, and only an X-ray tube rotates around a subject. This embodiment can be applied to either type. In this case, the rotate/rotate type will be exemplified.

In addition, the scan scheme of the X-ray CT apparatus according to this embodiment is targeted at ECG gated scanning. A scan target according to the embodiment is therefore the heart of a subject.

First Embodiment

FIG. 1 is a block diagram showing the arrangement of an X-ray CT apparatus according to the first embodiment. As shown in FIG. 1, the X-ray CT apparatus is equipped with a scan mechanism 10 and an image processing apparatus 30.

The scan mechanism 10 includes an annular or disk-like rotating frame 12. The rotating frame 12 supports an X-ray tube 14 and an X-ray detector 16 so as to allow them to rotate around a center axis Z of the rotating frame 12. The rotating frame 12 is connected to a rotation driving unit 18. The rotation driving unit 18 rotates the rotating frame 12 so as to rotate the X-ray tube 14 and the X-ray detector 16 around the center axis Z under the control of a scan control unit 44 in the image processing apparatus 30.

An FOV (Field Of View) is set inside the opening of the rotating frame 12. A top 20 on which a subject P is placed is inserted into the opening of the rotating frame 12. Typically, the subject P is placed on the top 20 such that the body axis of the subject P coincides with the Z-axis.

The X-ray tube 14 generates X-rays upon receiving a high voltage and a current from a high voltage generation unit 22. The high voltage generation unit 22 applies a high voltage to the X-ray tube 14 under the control of the scan control unit 44. More specifically, the X-ray tube 14 is equipped with an anode and a cathode. The high voltage generation unit 22 applies a tube voltage between the anode and the cathode. The cathode generates heat and emits thermoelectrons upon receiving a filament current from the high voltage generation unit 22. The emitted thermoelectrons collide with the anode due to the tube voltage. The collision of thermoelectrons with the anode generates X-rays. When thermoelectrons collide with the anode, a tube current flows in the X-ray tube 14. The intensity of X-rays to be generated is proportional to a tube current. The tube current is controlled by adjusting a filament current. Note that the X-ray tube 14 may be of a type that has a grid between the cathode and the anode. In this case, the high voltage generation unit 22 applies a voltage to the grid to control the tube current. These constituent elements for adjusting a tube current, e.g., a control means for adjusting a filament current and a control means for controlling the voltage of the grid, will be referred to as a tube current control unit.

The X-ray detector 16 detects the X-rays generated from the X-ray tube 14 and transmitted through the subject P, and generates an electrical signal corresponding to the intensity of the detected X-rays. A data acquisition circuit (DAS: Data Acquisition System) 24 is connected to the X-ray detector 16.

The data acquisition circuit 24 reads an electrical signal from the X-ray detector 16 under the control of the scan control unit 44. The data acquisition circuit 24 generates projection data (raw data) as a digital signal by amplifying the read electrical signal and converting the amplified electrical signal into digital signal. The generated projection data is supplied to the image processing apparatus 30.

An electrocardiograph 28 is connected to the image processing apparatus 30 wirelessly or via a wire or the like. The electrocardiograph 28 is attached to the subject P. The electrocardiograph 28 records an action potential accompanying the pulsation of the heart of the subject P and generates an electrocardiographic waveform representing a temporal change in action potential. In this case, the electrocardiograph 28 monitors an electrocardiographic waveform, and repeatedly generates a trigger signal originating from a specific phase in a cardiac cycle. For example, a specific phase is defined to an R-wave phase. A trigger signal originating from an R-wave phase will be referred to as an R trigger. The electrocardiograph 28 supplies the generated R trigger to the image processing apparatus 30. Note that in this embodiment, a specific phase is not limited to an R-wave phase and may be any phase.

As shown in FIG. 1, the image processing apparatus 30 includes an input unit 32, a preprocessing unit 34, a scan condition setting unit 36, an RR period calculation unit 38, an RR period determination unit 40, a time determination unit 42, a scan control unit 44, a reconstruction unit 46, a display unit 48, an operation unit 50, a storage unit 52, and a system control unit 54.

The input unit 32 repeatedly receives an R trigger from the electrocardiograph 28. At this time, the input unit 32 records the input time point of an R trigger.

The preprocessing unit 34 performs preprocessing such as logarithmic transformation and sensitivity correction for the projection data supplied from the data acquisition circuit 24. The storage unit 52 stores the preprocessed projection data.

The scan condition setting unit 36 sets a scan condition for ECG gated scanning. A scan condition is, for example, a condition concerning determination on the end of a scan. Such a scan condition is, for example, a scheduled scan time. A scheduled scan time is the upper limit of a scan period. A scheduled scan time is set to prevent, for example, the subject P from being excessively irradiated with X-rays. For example, the lower limit of a scheduled scan time is set to a time that makes it possible to reliably acquire projection data necessary and sufficient for the reconstruction of an image at a reconstruction target phase. The scan condition setting unit 36 calculates a scheduled scan time based on the heart rate (beat count per unit time) of the subject P measured by the electrocardiograph 28 before ECG gated scanning. More specifically, a scheduled scan time is defined on a beat count basis. A scheduled scan time is defined by a beat count at a given heart rate. This heart rate is set to a statistical value based on the heart rate of the subject P measured by the electrocardiograph 28 before ECG gated scanning. A statistical value is set to, for example, a maximum value, average value, or intermediate value. A beat count for defining a scheduled scan time will be referred to as a scheduled beat count hereinafter. In addition, the actual beat count from the start of a scan to the end of the scan will be referred to as an imaging beat count.

An RR period calculation unit 38 calculates, for each input of the latest R trigger, the period between the input time point of the latest R trigger of the R triggers repeatedly input to the input unit 32 and the input time point of the immediately preceding R trigger input to the input unit 32. The period between the input time points of temporally adjacent two R triggers will be referred to as an RR period hereinafter.

An RR period determination unit 40 compares the latest RR period with a threshold T to determine whether the latest RR period is equal to or more than the threshold T. The threshold T may be set to a time that makes it possible to acquire projection data necessary for the reconstruction of at least one set of image data. The threshold T is set to, for example, one beat period at a heart rate of 65 bpm. One beat period is the time interval required for one pulsation, e.g., an RR period.

The time determination unit 42 compares the elapsed time from the start time point of ECG gated scanning with a scheduled scan time to determine whether the scan elapsed time has exceeded the scheduled scan time. The elapsed time from the start time point of ECG gated scanning will be referred to as a scan elapsed time hereinafter. The time determination unit 42 measures the scan elapsed time from the start time point of ECG gated scanning in real time. If, for example, the RR period determination unit 40 determines that the latest RR period is not equal to or more than the threshold T, the time determination unit 42 determines that the scan elapsed time has exceeded the scheduled scan time.

The scan control unit 44 controls the rotation driving unit 18, the high voltage generation unit 22, and the data acquisition circuit 24 to perform a scan. More specifically, if the RR period determination unit 40 determines that the latest RR period is equal to more than the threshold T or the time determination unit 42 determines that the scan elapsed time is equal to or more than the scheduled scan time, the scan control unit 44 controls the rotation driving unit 18, the high voltage generation unit 22, and the data acquisition circuit 24 to terminate the scan. If the time determination unit 42 determines that the scan elapsed time is not equal to or more than the scheduled scan time, the scan control unit 44 controls the rotation driving unit 18, the high voltage generation unit 22, and the data acquisition circuit 24 to continue the scan.

The reconstruction unit 46 reconstructs image data concerning the subject P based on the acquired projection data. The storage unit 52 stores the image data.

The display unit 48 displays a display image corresponding to image data on a display device. The display unit 48 also displays, on the display device, a setting window for scan planning for ECG gated scanning. As a display unit, for example, a CRT display, liquid crystal display, organic EL display, plasma display, or the like can be used as needed.

The operation unit 50 accepts various kinds of instructions and information inputs from the operator via an input device. As an input device, a keyboard, a mouse, switches, and the like can be used.

The storage unit 52 stores projection data or image data having undergone preprocessing. The storage unit 52 stores a control program for the X-ray CT apparatus according to this embodiment. This control program is used to make the system control unit 54 execute the control function of the X-ray CT apparatus for the execution of ECG gated scanning.

The system control unit 54 functions as the main unit of the X-ray CT apparatus according to this embodiment. The system control unit 54 reads out control programs stored in the storage unit 52 and expands them in the memory, thereby controlling the respective units in accordance with the expanded control programs.

The details of the X-ray CT apparatus according to the first embodiment will be described next.

An image reconstruction method according to ECG gated scanning will be described first. ECG gated scanning is targeted at the fast moving heart. Importance is therefore attached to the time resolution of image data. As a reconstruction method used for ECG gated scanning, a half reconstruction method is mainly known.

The half reconstruction method is a method of reconstructing one set of image data based on the projection data set acquired while the rotating frame 12 rotates in a view range of 180°+α (fan angle). Half reconstruction is suitable for a case in which it is possible to acquire projection data corresponding to a view range of 180°+α in a period, of one heartbeat period, in which the movement of the heart is slow (e.g., a middiastole; a period in which the movement of the heart is relatively slow will be referred to as a stable period hereinafter). In the half reconstruction method, the time required for the rotating frame 12 to rotate in a view range of 180°+α is defined to the time resolution of image data to be reconstructed.

There is available a segment reconstruction method which aims at higher time resolution than the half reconstruction method. In the segment reconstruction method, a view range of 180°+α is segmented into a plurality of segments. This method then acquires a plurality of projection data sets respectively corresponding to a plurality of segments throughout a plurality of consecutive or separate heartbeats. The method reconstructs one set of image data based on a plurality of projection data sets. As described above, the segment reconstruction method is suitable for a case in which it is impossible to acquire projection data corresponding to a view range of 180°+α in a stable period of one heartbeat period. In the segment reconstruction method, the shortest time required for the rotating frame 12 to rotate in a view range corresponding to (180°+α)/number of segments is defined to a time resolution.

Note that the reconstruction method according to this embodiment can also be applied to a full reconstruction method of acquiring projection data in a view range of 360°. When acquiring projection data in a view range of 360°, it is possible to apply the segment reconstruction method as in the case of the half reconstruction method.

A basic sequence for ECG gated scanning according to this embodiment will be described next with reference to FIG. 2. FIG. 2 shows a scan sequence for ECG gated scanning. Referring to FIG. 2, assume that the scheduled beat count is set to 2. That is, the operator estimates that since the heart rate of the subject is relatively high, it is impossible to acquire projection data necessary and sufficient for reconstruction by one beat. Assume that X-rays are continuously generated.

First of all, the input unit 32 repeatedly receives R triggers from the electrocardiograph 28 before the start of the generation of X-rays. The scan control unit 44 controls the high voltage generation unit 22 to start generating X-rays at the moment when the elapsed time from the input time point of a predetermined R trigger (the first R trigger) exceeds a defined irradiation wait period. The high voltage generation unit 22 applies a tube voltage to the X-ray tube 14 and supplies a filament current to it under the control of the scan control unit 44. Upon receiving the tube voltage and the filament current, the X-ray tube 14 generates X-rays. The irradiation wait period is defined to the time from the input time point of the first R trigger to the instant the X-ray tube 14 actually generates X-rays. As will be described later, a scan starts from the input time point of the next R trigger (the second R trigger). An irradiation wait period is therefore set to make the X-ray tube 14 generate X-rays by the input time point of the second R trigger. In practice, since the energy of X-rays is not stable from the start time when they are generated, an irradiation wait period is set to be shorter than, for example, the RR period.

At the input time point of the next R trigger (the second R trigger), the scan control unit 44 starts a scan. During the scan, the scan control unit 44 controls the rotation driving unit 18 to repeatedly rotate the rotating frame 12, and controls the data acquisition circuit 24 to repeatedly acquire projection data (raw data). The scan control unit 44 terminates the scan at the moment when the scan elapsed time exceeds the scheduled scan time. For example, the scan control unit 44 controls the high voltage generation unit 22 to terminate the generation of X-rays. The high voltage generation unit 22 finishes applying a tube voltage to the X-ray tube 14 and supplying a filament current to it under the control of the scan control unit 44. This makes the X-ray tube 14 finish generating X-rays. Note that the X-ray tube 14 may rotate and the data acquisition circuit 24 may acquire projection data from the time before the generation of X-rays.

During a scan, as shown in FIG. 2, the heart rate of the subject P sometimes decreases to a rate that makes it possible to acquire projection data necessary and sufficient for reconstruction by only one beat. Referring to FIG. 2, the apparatus sometimes acquires sufficient projection data in the RR period between the input time point of the second R trigger and the input time point of the third R trigger. In this case, the X-rays applied from the input time point of the R trigger (the third R trigger) input for the first time after the start of a scan to the end of the scheduled scan time do not contribute to image reconstruction.

Upon determining that data necessary and sufficient for reconstruction have been acquired, the X-ray CT apparatus according to the first embodiment terminates the scan before the scheduled scan time elapses.

Figure 3:
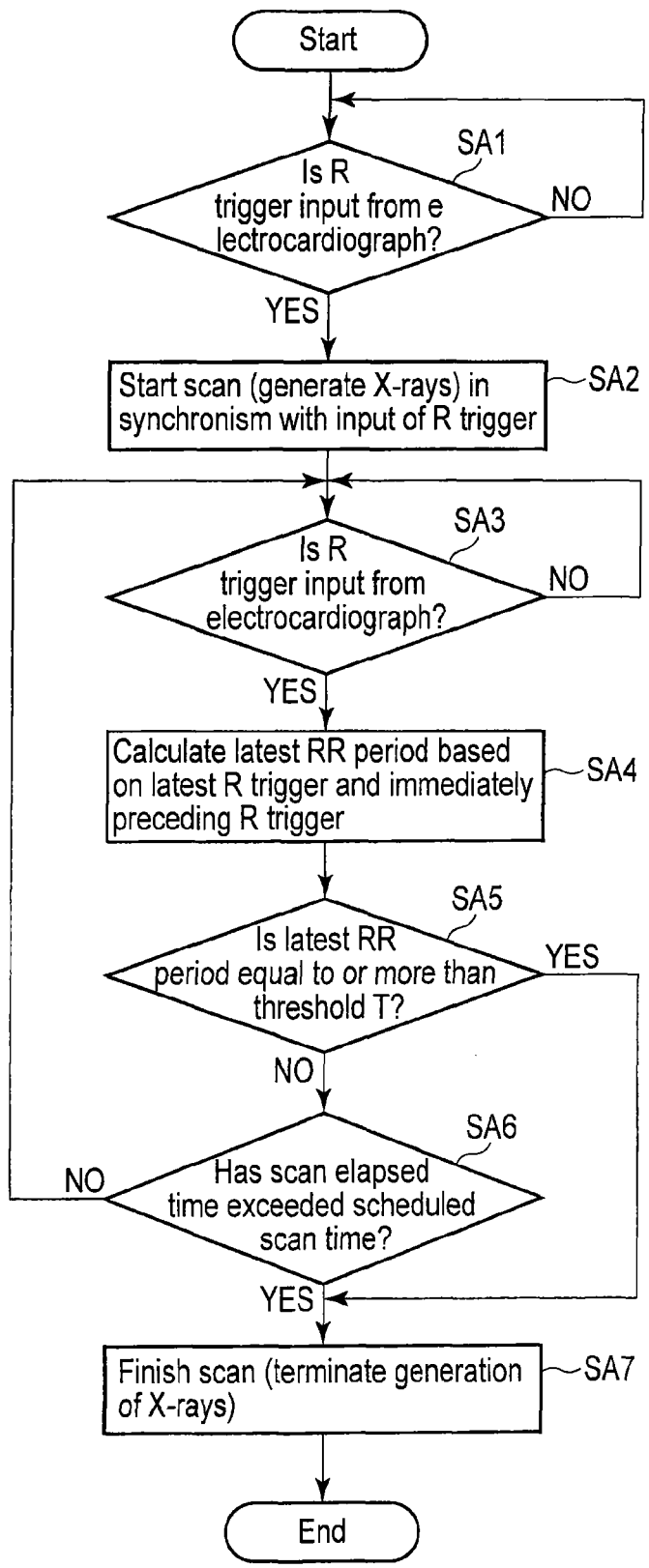
FIG. 3 is a flowchart showing a typical procedure for ECG gated scanning performed by a system control unit in FIG. 1.

FIG. 3 shows a typical procedure for ECG gated scanning performed under the control of the system control unit 54 according to the first embodiment.

Note that ECG gated scanning according to the first embodiment can be applied to any X-ray irradiation modes. For example, there are three X-ray irradiation modes including a continuous irradiation mode, a tube current modulation irradiation mode, and an ON/OFF modulation irradiation (intermittent irradiation) mode. In the continuous irradiation mode, the high voltage generation unit 22 supplies a filament current to the X-ray tube 14 and applies a tube voltage to it so as to make a tube current flowing in the X-ray tube 14 constant. That is, in the continuous irradiation mode, constant-energy X-rays are continuously generated. In the tube current modulation irradiation mode, the high voltage generation unit 22 supplies a filament current to the X-ray tube 14 and applies a tube voltage to it so as to alternately switch the tube current between the first and second tube current values. The first tube current value is set to a value that makes it possible to obtain sufficient image quality. The second tube current value is set to a value smaller than the first tube current value. That is, in the tube current modulation irradiation mode, the apparatus alternately generates X-rays with a standard energy and X-rays with a lower energy. In the ON/OFF modulation irradiation mode, the high voltage generation unit 22 supplies a filament current to the X-ray tube 14 and applies a tube voltage to it so as to alternately generate and stop generating X-rays.

As shown in FIG. 3, before the start of a scan, the system control unit 54 waits for the input of an R trigger for the start of a scan (e.g., the second R trigger in FIG. 2) to the input unit 32 (step SA1). Assume that at the stage before step SA1, as in FIG. 2, an R trigger for the generation of X-rays (the first R trigger in FIG. 2) has been input to the input unit 32 before the input of the above R trigger.

In step SA1, when an R trigger is input (YES in step SA1), the system control unit 54 controls the scan control unit 44 to start a scan (step SA2). In step SA1, the scan control unit 44 starts a scan in synchronism with the input of this R trigger to the input unit 32, as shown in FIG. 2. In this case, to perform a scan is to generate X-rays for the acquisition of projection data for image data reconstruction, rotate the rotating frame 12, and acquire projection data. More specifically, the scan control unit 44 controls the high voltage generation unit 22 based on the input of an R trigger to make the X-ray tube 14 generate X-rays. The scan control unit 44 also controls the rotation driving unit 18 based on the input of an R trigger to rotate the rotating frame 12. In addition, the scan control unit 44 controls the data acquisition circuit 24 based on the input of the second R trigger to acquire projection data (raw data). The storage unit 52 stores the acquired projection data. The input unit 32 records the input time point of the R trigger input in step SA1 as a scan start time point. The time determination unit 42 measures the scan elapsed time from the scan start time point for step SA6 (to be described later).

Upon performing step SA2, the system control unit 54 waits for the input of an R trigger from the electrocardiograph via the input unit 32 (step SA3).

Upon receiving an R trigger in step SA3, the system control unit 54 causes the RR period calculation unit 38 to perform calculation processing (step SA4). In step SA4, the RR period calculation unit 38 calculates the latest RR period based on the input time point of the latest R trigger and the input time point of the immediately preceding R trigger. In first step SA4, the latest R trigger is the R trigger input in latest step SA3, and the immediately preceding R trigger is the R trigger input in step SA1. In second and subsequent step SA4, the latest R trigger is the R trigger input in step SA3, and the immediately preceding R trigger is the R trigger input in step SA3 immediately preceding latest step SA3. More specifically, the RR period calculation unit 38 calculates the latest RR period based on the input time point of the latest R trigger and the input time point of the immediately preceding R trigger.

Upon performing step SA4, the system control unit 54 causes the RR period determination unit 40 to perform determination processing (step SA5). In step SA5, the RR period determination unit 40 compares the latest RR period with the threshold T to determine whether the latest RR period is equal to or more than the threshold T.

Upon determining in step SA5 that the latest RR period is equal to or more than the threshold T (NO in step SA5), the system control unit 54 causes the time determination unit 42 to perform determination processing (step SA6). In step SA6, the time determination unit 42 compares the scan elapsed time with the scheduled scan time to determine whether the scan elapsed time has exceeded the scheduled scan time.

Upon determining in step SA6 that the scan elapsed time has not exceeded the scheduled scan time (NO in step SA6), the system control unit 54 returns to step SA3 to continue the scan. Note that the determination processing in step SA6 is repeated until the input of the next R trigger.

Upon determining in step SA5 that the latest RR period is equal to or more than the threshold T (YES in step SA5) or determining in step SA6 that the scan elapsed time has exceeded the scheduled scan time (YES in step SA6), the system control unit 54 causes the scan control unit 44 to perform termination processing (step SA7). In step SA7, the scan control unit 44 controls the rotation driving unit 18, the high voltage generation unit 22, and the data acquisition circuit 24 to terminate the scan. The high voltage generation unit 22 stops applying a high voltage to the X-ray tube 14 and supplying a filament current to it under the control of the scan control unit 44. This makes the X-ray tube 14 finish generating X-rays. The rotation driving unit 18 also finishes rotating the rotating frame 12 under the control of the scan control unit 44. The data acquisition circuit 24 finishes acquiring projection data under the control of the scan control unit 44. Note that it is not necessary to perform scan termination processing immediately after the scan elapsed time exceeds the scheduled scan time. For example, scan termination processing may be performed after the lapse of a predetermined margin time since the elapsed time has exceeded the scheduled scan time. Providing a margin time can prevent a situation in which projection data necessary for reconstruction cannot be acquired.

Upon performing step SA7, the apparatus terminates the ECG gated scanning according to the first embodiment.

Figure 4:
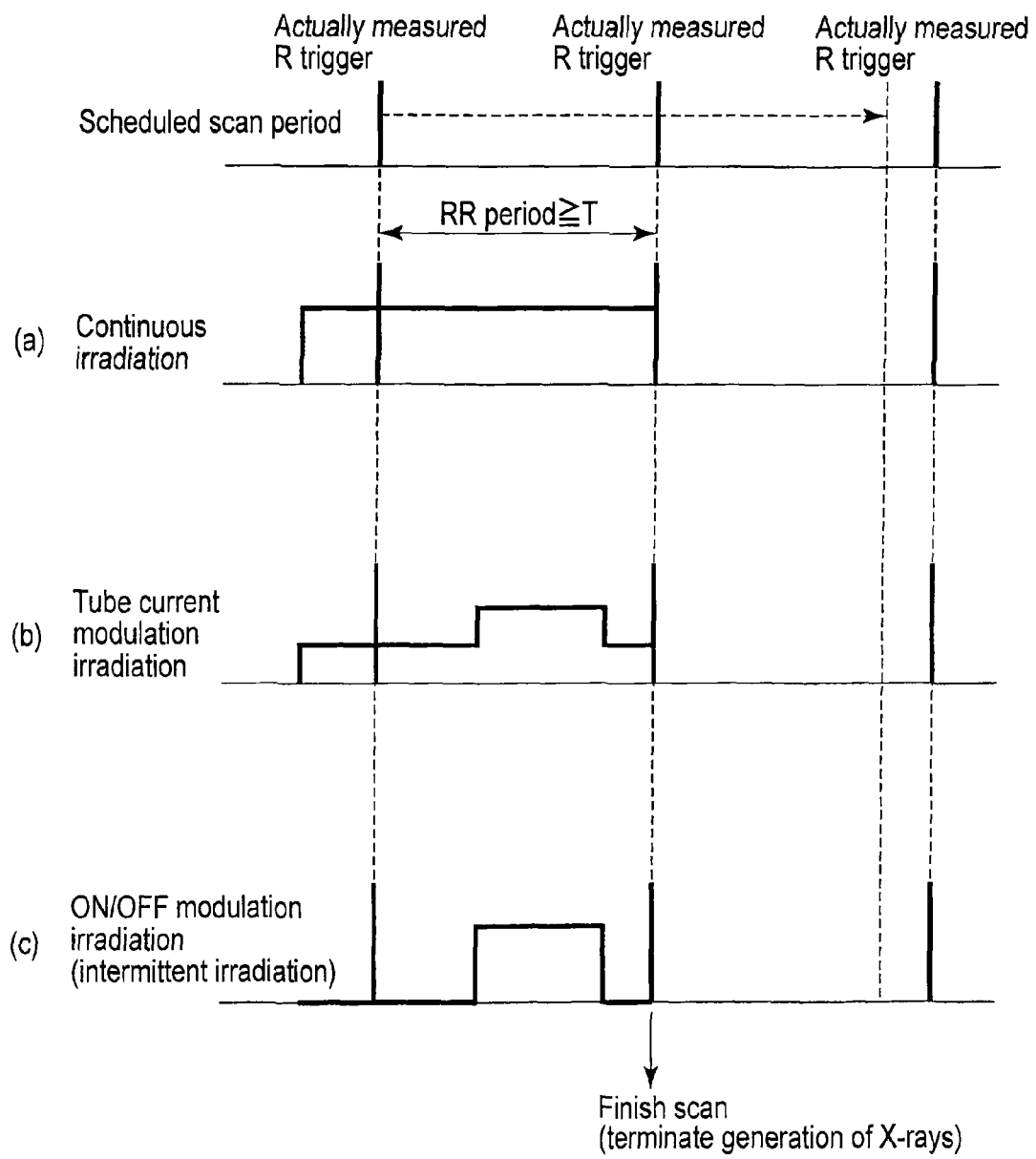
FIG. 4 is a chart for schematically explaining ECG gated scanning in FIG. 3.

As described above, the system control unit 54 determines in step SA3 whether the latest RR period is equal to or more than the threshold T. The threshold T is set to the time that makes it possible to acquire projection data necessary for the reconstruction of at least one set of image data. It is therefore estimated, from the fact that the latest RR period is equal to or more than the threshold T, that projection data necessary and sufficient for image reconstruction have been acquired in the latest one beat period. Upon determining in step SA5 that the latest RR period is equal to or more than the threshold T, the system control unit 54 terminates the scan. If, for example, as shown in FIG. 4, the RR period concerting the first beat period (the period between the input time point of the first R trigger and the input time point of the second R trigger), the system control unit 54 terminates the scan upon receiving the second R trigger. In this case, the scan elapsed time is made shorter than the scheduled scan time. In other words, the imaging beat count is decreased in accordance with an actual RR period during a scan period. This makes it possible to avoid X-ray irradiation which does not contribute to image reconstruction, and hence to reduce the radiation dosage of the subject P. In addition, since it is possible to shorten the scan time for one scan, the examination throughput improves.

Figure 5:
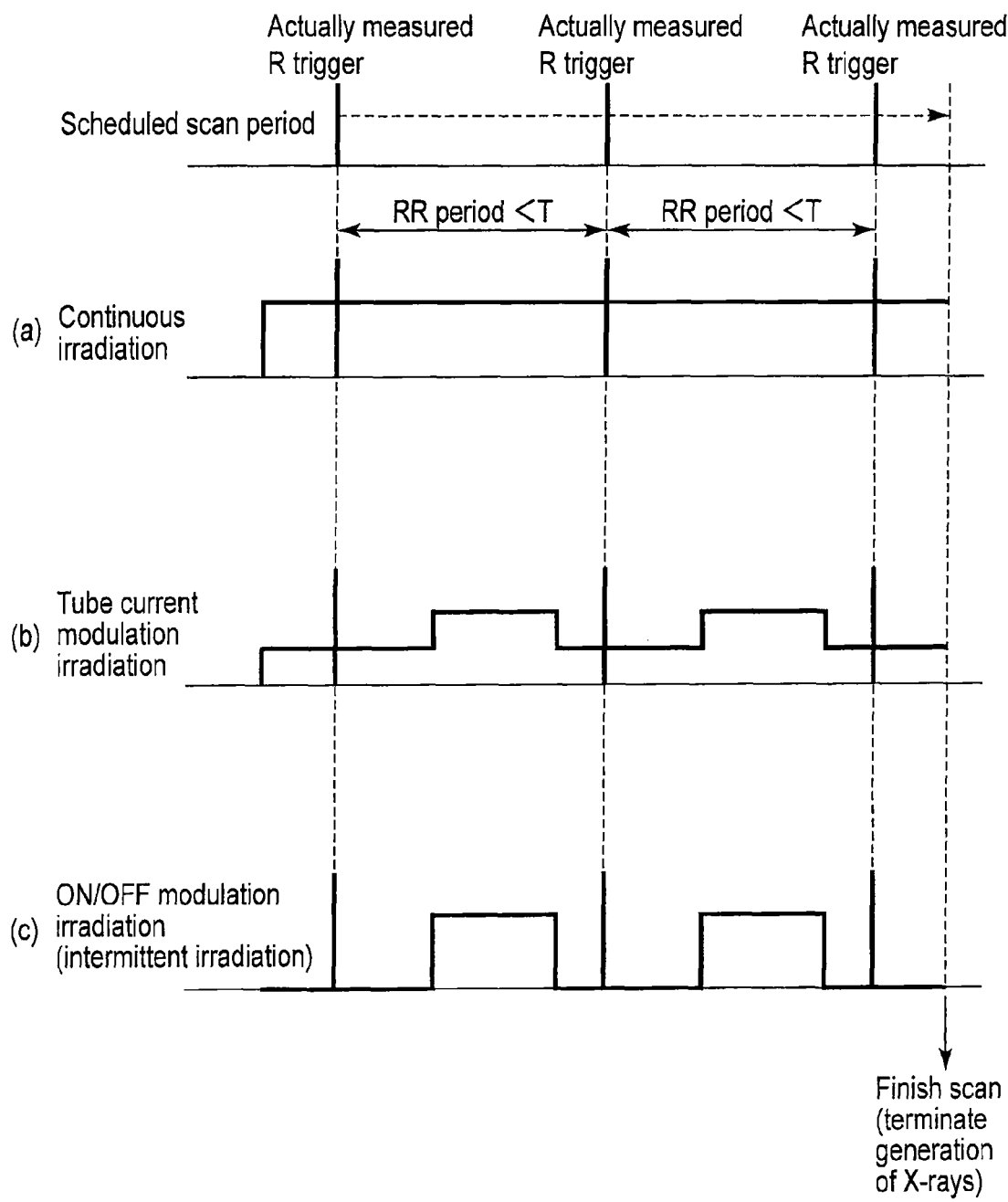
FIG. 5 is another chart for schematically explaining ECG gated scanning in FIG. 3.

If the latest RR period is equal to or more than the threshold T, it is estimated that projection data necessary and sufficient for image reconstruction have not been acquired in the latest one beat period. If, therefore, the system control unit 54 determines in step SA5 that the latest RR period is not equal to or more than the threshold T, the scan should not be terminated. In this case, the system control unit 54 in step SA6 whether the scan elapsed time exceeds the scheduled scan time. As described above, the scheduled scan time is set to the time that is longer than the threshold T and makes it possible to reliably acquire projection data necessary and sufficient for the reconstruction of at least one set of image data. If the system control unit 54 determines in step SA6 that the scan elapsed time has not exceeded the scheduled scan time, since necessary and sufficient projection data have not been acquired, the scan should be continued. In this case, therefore, the process returns to step SA3 to continue the scan to wait again for the input of the latest R trigger. If the system control unit 54 determines in step SA6 that the scan elapsed time has exceeded the scheduled scan time, even if the latest RR period is not equal to or more than the threshold T, it is estimated that necessary and sufficient have been acquired. In this case, the system control unit 54 terminates the scan. Consider, for example, a case in which the scheduled beat count is 2, as shown in FIG. 5. If the RR period concerning the first beat period and the RR period concerning the second beat period are equal to or more than the threshold T, the system control unit 54 terminates the scan when the scan elapsed time reaches the scheduled scan time. In this case, the scan elapsed time almost coincides with the scheduled scan time. That is, it can be said that the apparatus has performed the scan as scheduled.

The system control unit 54 repeats steps SA3 to SA6 until determining in step SA5 that the latest RR period is equal to or more than the threshold T or determining in step SA6 that the scan elapsed time has exceeded the scheduled scan time. The system control unit 54 repeats steps SA3 to SA6 until determining from the latest RR period or the elapsed time that projection data necessary for image reconstruction have been acquired. If the RR period condition in step SA5 or the scan time condition in step SA6 is satisfied, the system control unit 54 terminates the scan in step SA7.

Upon completion of the scan, the reconstruction unit 46 reconstructs image data based on the projection data acquired in the scan period. Upon completion of only a scan corresponding to one beat period, the reconstruction unit 46 executes half reconstruction. Upon completion of a scan corresponding to a plurality of beat periods, the reconstruction unit 46 performs segment reconstruction. More specifically, when performing half reconstruction, the reconstruction unit 46 executes half reconstruction processing for the projection data acquired in one beat period to generate image data concerning the subject P. When performing segment reconstruction, the reconstruction unit 46 executes segment reconstruction processing for the projection data acquired in each beat period to generate image data concerning the subject P. The display unit 48 displays a display image corresponding to the generated image data.

According to the above description, ECG gated scanning according to the first embodiment can implement ALAR (As Low As Reasonably practicable) exposure, i.e., minimum exposure. In addition, according to ECG gated scanning according to the first embodiment, when the RR period becomes longer than the RR period based on the standard heart rate at the time of a scan (the heart rate is lower than the standard heart rate), the apparatus terminates the scan at the input time point of the latest R trigger, even if the actual elapsed time has not exceeded the scheduled scan time. That is, when performing scan planning, the operator can set a scheduled scan time to a relatively long time without regard to radiation dosage. This makes it possible to simply execute scan planning. In addition, when reconstructing image data by the half reconstruction method instead of the segment reconstruction method in ECG gated scanning according to the first embodiment, it is possible to continue a scan until the latest RR period exceeds the threshold T, by setting a scheduled scan time to a relatively long time.

As described above, therefore, the X-ray CT apparatus according to the first embodiment can improve the scan efficiency concerning ECG gated scanning.

Second Embodiment

In the first embodiment, if the time determination unit 42 determines that the scan elapsed time is equal to or more than the scheduled scan time, the scan control unit 44 terminates the scan, even if the RR period is not equal to or more than a threshold. However, this embodiment is not limited to this. The scan control unit 44 may decide the timing of terminating a scan in accordance with other scan condition different from a scheduled scan time. Another scan condition is, for example, a scheduled X-ray irradiation time. A scan control unit 44 according to the second embodiment terminates a scan if the RR period is not equal to or more than a threshold and the total X-ray irradiation time in one examination is equal to or more than a scheduled irradiation time. An X-ray computed tomography apparatus according to the second embodiment will be described below. Note that the same reference numerals in the following description denote constituent elements having almost the same functions as in the first embodiment, and a repetitive description will be made only when required.

A scan condition setting unit 36 according to the second embodiment sets a scheduled X-ray irradiation time in accordance with an instruction input by the user via an operation unit 50. A scheduled irradiation time is defined to the upper limit of the total X-ray irradiation time for the subject P. A scheduled irradiation time is set to prevent a subject from being excessively exposed to X-rays. The lower limit of a scheduled irradiation time is set to the time that makes it possible to reliably acquire projection data necessary and sufficient for image reconstruction at a reconstruction target phase.

A time determination unit 42 according to the second embodiment compares the actual total X-ray irradiation time of an X-ray tube 14 with a scheduled irradiation time to determine whether the X-ray irradiation time has exceeded the scheduled irradiation time. The time determination unit 42 measures the total irradiation time from the start of X-ray irradiation. If, for example, an RR period determination unit 40 determines that the latest RR period is not equal to or more than a threshold T, the time determination unit 42 determines whether the total irradiation time has exceeded the scheduled irradiation time.

If the RR period determination unit 40 determines that the latest RR period is equal to or more than the threshold T or the time determination unit 42 determines that the total irradiation time is equal to or more than the scheduled irradiation time, the scan control unit 44 according to the second embodiment controls a rotation driving unit 18, a high voltage generation unit 22, and a data acquisition circuit 24 so as to terminate the scan. In addition, if the time determination unit 42 determines that the total irradiation time is not equal to or more than the scheduled irradiation time, the scan control unit 44 controls the rotation driving unit 18, the high voltage generation unit 22, and the data acquisition circuit 24 so as to continue the scan.

ECG gated scanning performed under the control a system control unit 54 according to the second embodiment will be described next. FIG. 6 is a flowchart showing a typical procedure for ECG gated scanning performed under the control of the system control unit 54 according to the second embodiment. The same reference numerals denote steps of the same processing contents as those in ECG gated scanning in FIG. 3, and a description of them will be omitted.

As shown in FIG. 6, if the RR period determination unit 40 determines in step SA5 that the latest RR period is not equal to or more than the threshold T (NO in step SA5), the system control unit 54 causes the time determination unit 42 to perform determination processing (step SD6). In step SD6, the time determination unit 42 compares the total irradiation time with the scheduled irradiation time to determine whether the total irradiation time has exceeded the scheduled irradiation time.

If the time determination unit 42 determines in step SD6 that the total irradiation time has not exceeded the scheduled irradiation time (NO in step SD6), the system control unit 54 returns to step SA3 to continue the scan. Note that the time determination unit 42 repeats the determination processing in step SD6 until the next R trigger is input.

If the RR period determination unit 40 determines in step SA5 that the latest RR period is equal to or more than the threshold T (YES in step SA5) or the time determination unit 42 determines in step SD6 that the total irradiation time has exceeded the scheduled irradiation time (YES in step SD6), the system control unit 54 causes the scan control unit 44 to perform termination processing (step SA7). Note that the apparatus may not perform termination processing for a scan immediately after the total irradiation time has exceeded the scheduled irradiation time. For example, the apparatus may perform terminal processing for a scan after the lapse of a predetermined margin time since the time point when the total irradiation time has exceeded the scheduled irradiation time. Providing a margin time can prevent a situation in which projection data necessary for reconstruction cannot be acquired.

Upon performing step SA7, the apparatus terminates ECG gated scanning according to the second embodiment.

As described above, the X-ray CT apparatus according to the second embodiment can forcibly terminate a scan at the moment when the total irradiation time exceeds the upper limit value, even if the RR period is not equal to or more than the upper limit value. This can prevent the subject from being excessively exposed to X-rays.

The X-ray CT apparatus according to the second embodiment can improve the scan efficiency concerning ECG gated scanning.

As described above, a determination target for the time determination unit 42 is a scan elapsed time in the first embodiment, and a total irradiation time in the second embodiment. The user can arbitrarily select a determination target for the time determination unit 42 between a scan elapsed time and a total irradiation time via the operation unit 50.

Third Embodiment

In the first and second embodiments, when the latest RR period is equal to or more than the threshold T, the apparatus terminates a scan. In the third embodiment, if the latest RR period is equal to or more than the threshold T, the apparatus determines whether projection data which can be substantially used for reconstruction. If projection data which can be substantially used for reconstruction have been acquired, the apparatus terminates the scan. An X-ray CT apparatus according to the third embodiment will be described. Note that the same reference numerals in the following description denote constituent elements having almost the same functions as in the first and second embodiments, and a repetitive description will be made only when required.

FIG. 7 is a block diagram showing the arrangement of the X-ray CT apparatus according to the third embodiment. As shown in FIG. 7, the X-ray CT apparatus according to the third embodiment includes a valid beat determination unit 56.

If an RR period determination unit 40 determines that the latest RR period is equal to or more than the threshold T, the valid beat determination unit 56 determines whether a valid beat condition is satisfied. A valid beat condition is defined to whether projection data which can be substantially used for reconstruction have been acquired in the latest one beat period. If the valid beat condition is satisfied, the valid beat determination unit 56 confirms that the beat is valid. If the valid beat condition is not satisfied, the valid beat determination unit 56 confirms that the beat is invalid.

If the valid beat determination unit 56 determines that the valid beat condition is not satisfied, a time determination unit 42 determines whether the scan elapsed time has reached a scheduled scan time or the total irradiation time has reached a scheduled irradiation time.

If the valid beat determination unit 56 determines that the valid beat condition is satisfied or the time determination unit 42 determines that the scan elapsed time has exceeded the scheduled scan time (or the total irradiation time has exceeded the scheduled irradiation time), a scan control unit 44 controls a rotation driving unit 18, a high voltage generation unit 22, and a data acquisition circuit 24 so as to terminate the scan. If the valid beat determination unit 56 determines that the valid beat condition is not satisfied and the time determination unit 42 determines that the scan elapsed time has not exceeded the scheduled scan time (or the total irradiation time has not exceeded the scheduled irradiation time), the scan control unit 44 controls the rotation driving unit 18, the high voltage generation unit 22, and the data acquisition circuit 24 so as to continue the scan.

ECG gated scanning according to the third embodiment will be described in detail next.

In ECG gated scanning, a scan condition setting unit 36 sets a reconstruction target phase (to be referred to as a reconstruction phase hereinafter). In order to reconstruct image data at a reconstruction phase, for example, the apparatus executes a scan so as to acquire projection data which can be substantially used in a time range including a reconstruction phase (to be referred to as a reconstruction use range hereinafter). For example, a reconstruction use range is set to a time range of ±5% centered on a reconstruction phase. A reconstruction use range is typically set to a period in which the movement of the heart is relatively slow.

Figure 8:
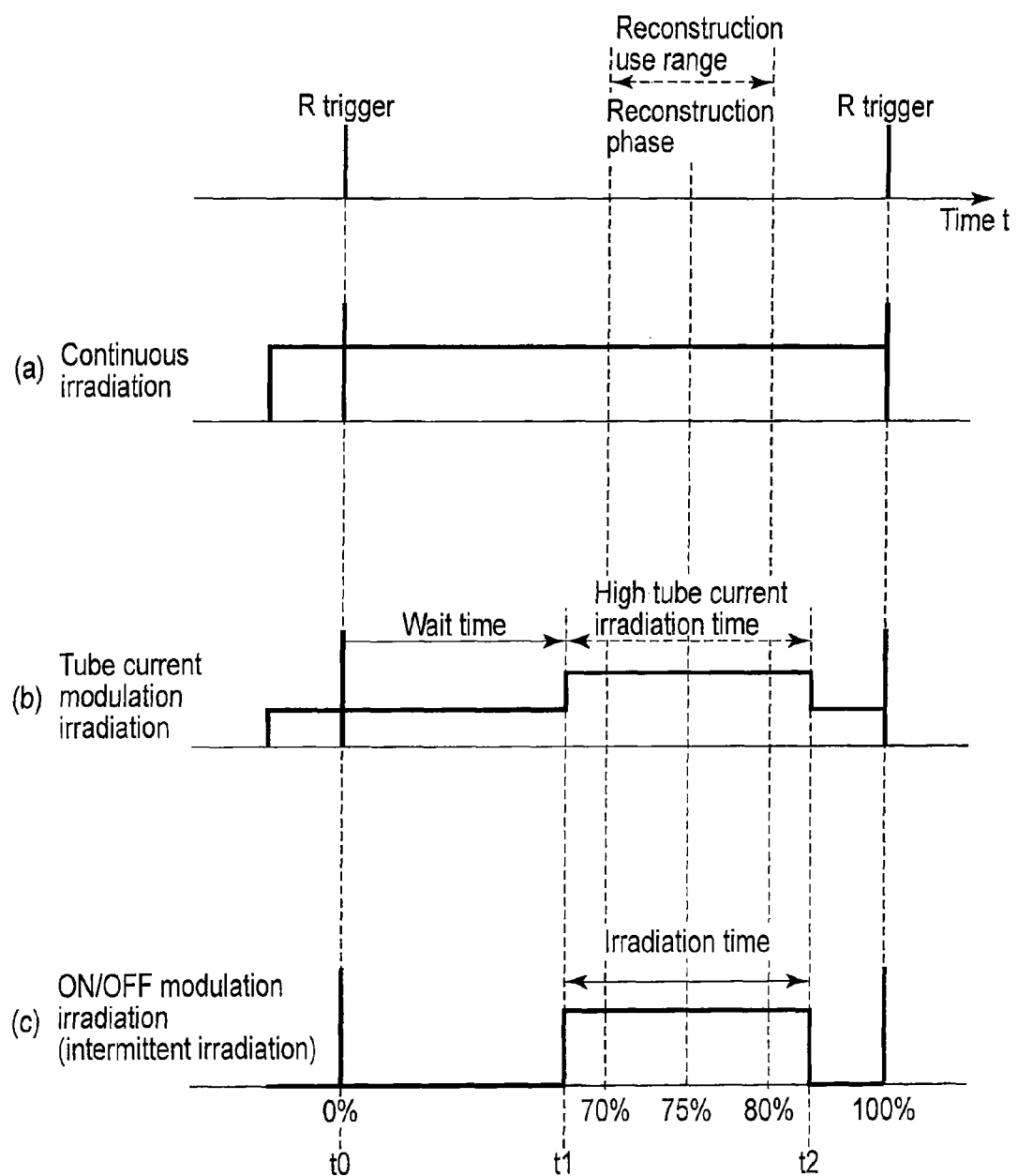
FIG. 8 is a chart showing the temporal relationship between irradiation period in each X-ray irradiation mode, reconstruction use range, and reconstruction phase according to the third embodiment.

FIG. 8 is a chart showing the temporal relationship between irradiation period in each X-ray irradiation mode, reconstruction use range, and reconstruction phase. Assume that, as shown in FIG. 8, a reconstruction phase is set to 75%, and a reconstruction use range is set to 70% to 80%.

In the continuous irradiation mode, the apparatus applies X-rays with a tube current having a constant tube current value until an instruction to terminate the generation of X-rays is issued. This tube current value corresponds to the energy value of X-rays which can generate projection data which can be substantially used for reconstruction. Consequently, in the continuous irradiation mode, projection data acquired in a reconstruction use range can be substantially used for reconstruction. Note that projection data which can be substantially used for reconstruction are projection data which can generate image data having sufficient image quality.

In the tube current modulation irradiation mode, basically, the apparatus continuously generates X-rays with a tube current having a low tube current value. In addition, settings are made in the apparatus to switch from a lower tube current value to a high tube current value at the moment when a wait period has elapsed since input time point t0 of an R trigger. In the case shown in FIG. 8, the apparatus switches from a low tube current value to a high tube current value at time t1. The low tube current value corresponds to the energy value of X-rays which cannot generate projection data which can be substantially used for reconstruction. The high tube current value corresponds to the energy value of X-rays which can generate projection data which can be substantially used for reconstruction. To improve image quality, it is preferable to reconstruct image data based on projection data originating from X-rays with the high tube current value. Therefore, a high tube current irradiation time is set so as to include a reconstruction use range. The apparatus switches from a high tube current to a low tube current at the moment when the high tube current irradiation time has elapsed since switching time t1. In the case shown in FIG. 8, the apparatus switches from the high tube current value to the low tube current value at time t2. For example, a high tube current irradiation time is set to a period corresponding to a reconstruction use range. If, for example, the reconstruction use range is 70% to 80%, a high tube current irradiation time is set to a period corresponding to 10% between 70% and 80%.

In the ON/OFF modulation irradiation mode, basically, the apparatus generates no X-rays. Settings are made in the apparatus so as to be switched on to generate X-rays at the moment when a wait period has elapsed since input time point t0 of an R trigger. The apparatus is switched off so as not to generate X-rays at the moment when an irradiation time has elapsed since switching time t1. An irradiation time is set to, for example, a period corresponding to a reconstruction use range. If, for example, the reconstruction use range is 70% to 80%, the irradiation time is set to a period including a period corresponding to 10% between 70% and 80%.

In practice, the standard heart rate used for planning differs from an actual heart rate at the time of a scan. If the actual RR period is smaller than the threshold T, the apparatus continues the scan as described in the first and second embodiments. If the actual RR period is larger than the threshold T, the apparatus finishes generating X-rays in the first and second embodiments. Even if, however, the actual RR period is larger than the threshold T, the apparatus sometimes has not acquired necessary and sufficient projection data which can be substantially used for the reconstruction of image data at a reconstruction phase depending on the tube current modulation irradiation mode and the ON/OFF modulation irradiation mode.

FIG. 9 is a view showing a valid beat condition for each X-ray irradiation mode. As shown in FIG. 9, in the continuous irradiation mode, no valid beat conditions is set. That is, if the latest RR period is equal to or more than the threshold T, the valid beat condition is unconditionally satisfied to finish generating X-rays. In the tube current modulation irradiation mode and the ON/OFF modulation irradiation mode, valid beat conditions are set. In the tube current modulation irradiation mode, if X-rays are not applied with a high tube current at a reconstruction phase, image data at the reconstruction phase deteriorates. The valid beat condition in the tube current modulation irradiation mode is therefore set to whether X-rays are applied with a high tube current at a reconstruction phase. In the ON/OFF modulation irradiation mode, if no X-rays are applied at a reconstruction phase, image data at the reconstruction phase deteriorates. The termination condition for the ON/OFF modulation irradiation mode is set to whether X-rays are applied at a reconstruction phase.

Figure 10:
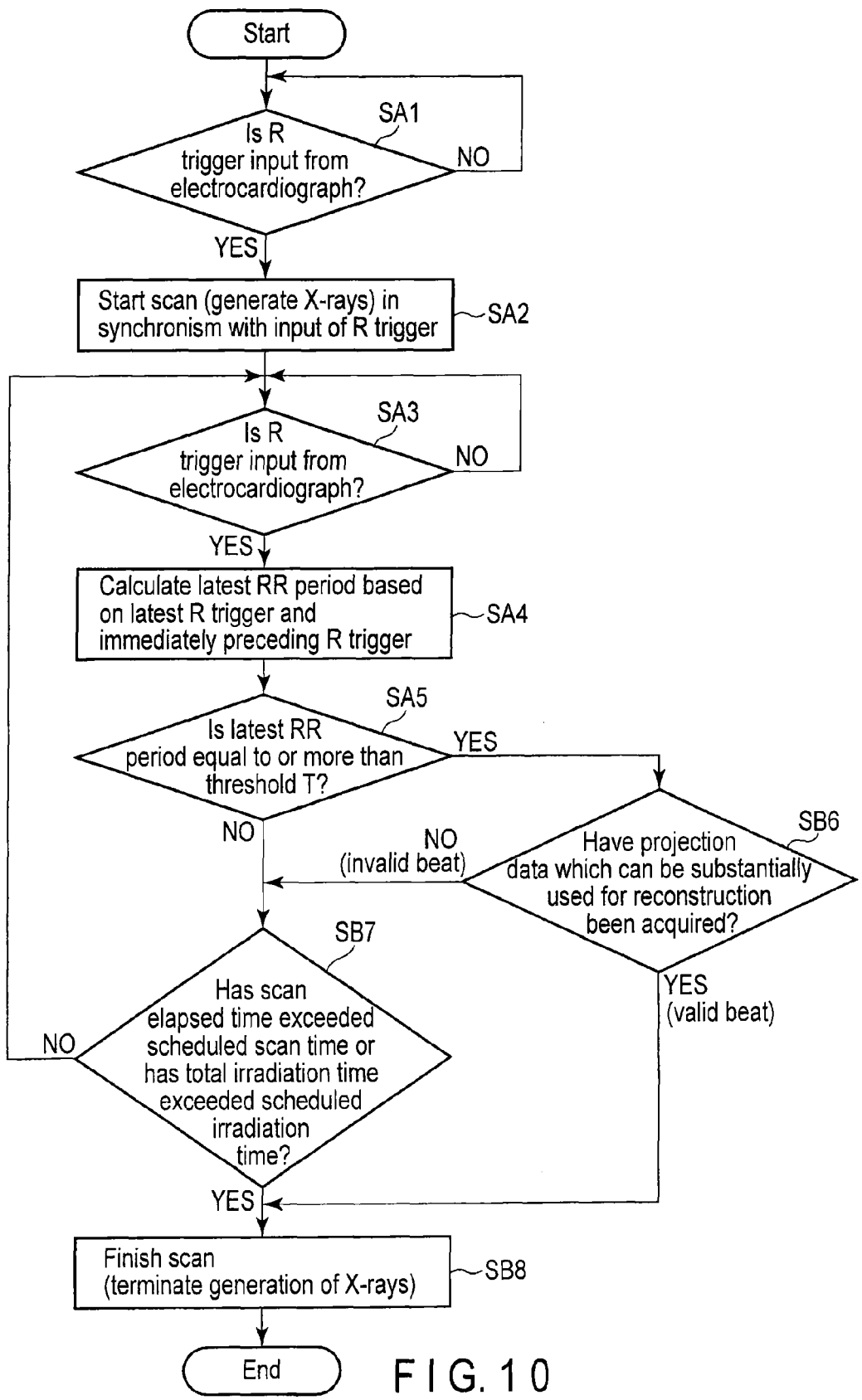
FIG. 10 is a flowchart showing a typical procedure for ECG gated scanning performed by a system control unit in FIG. 7.

FIG. 10 a flowchart showing a typical procedure for ECG gated scanning performed under the control of a system control unit 54 according to the third embodiment. Note that the same reference numerals denote steps of the same processing contents as those in ECG gated scanning in FIGS. 3 and 6, and a description of them will be omitted.

If the RR period determination unit 40 determines in step SA5 that the latest RR period is equal to or more than the threshold T (YES in step SA5), the system control unit 54 causes the valid beat determination unit 56 to perform determination processing (step SB6). The valid beat determination unit 56 determines in step SB6 whether a valid beat condition corresponding to the X-ray irradiation mode is satisfied, i.e., whether necessary and sufficient projection data which can be substantially used for the reconstruction of image data at a reconstruction phase have been acquired.

As described above, if the X-ray irradiation mode is the continuous irradiation mode, the valid beat determination unit 56 determines that the termination condition is satisfied. In the tube current modulation irradiation mode, the valid beat determination unit 56 determines whether X-rays have been applied with a high tube current at a preset reconstruction phase. In the ON/OFF modulation irradiation mode, the valid beat determination unit 56 determines whether X-rays have been applied at a preset reconstruction phase. Specific processing in step SB6 in the tube current modulation irradiation mode will be described below.

Figure 11:
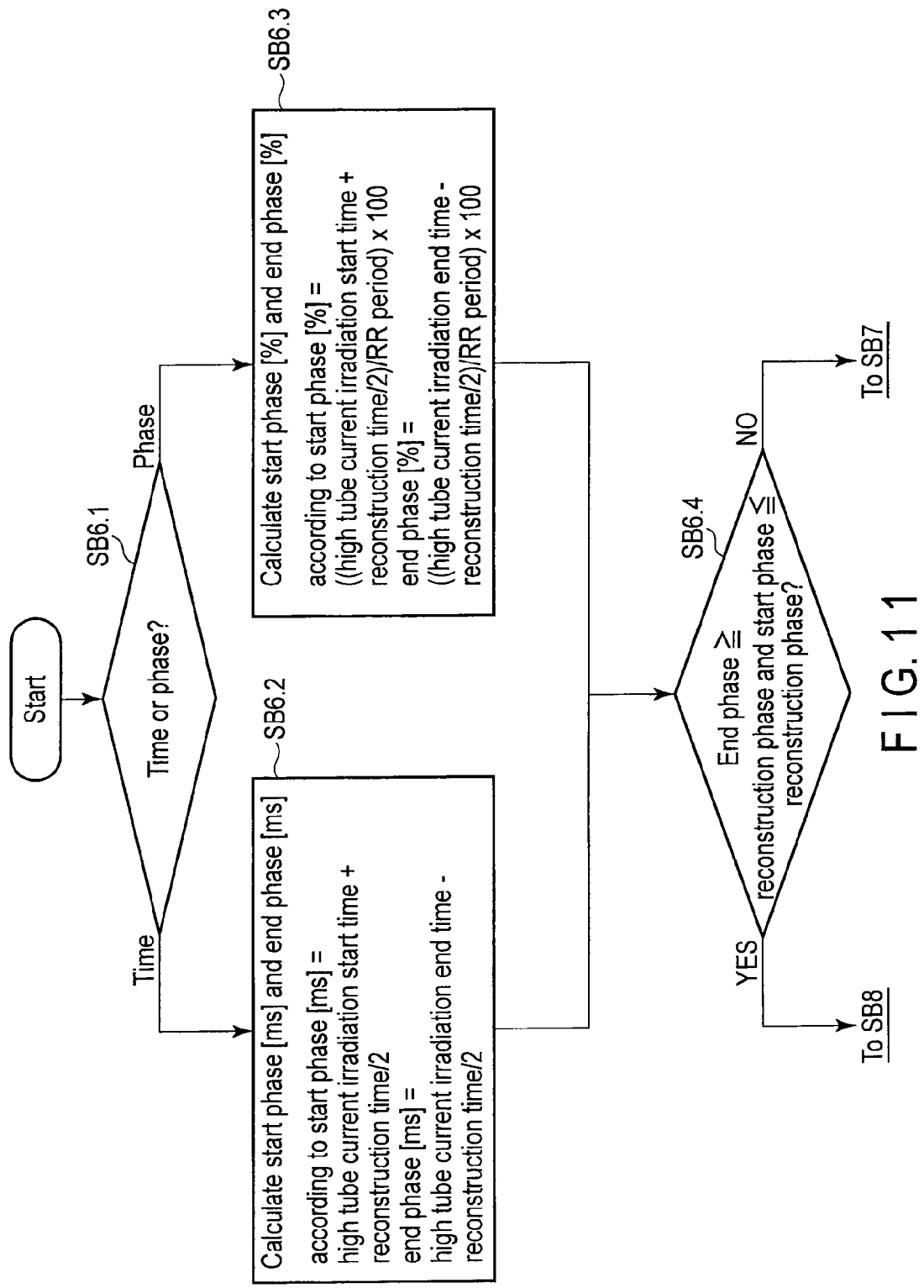
FIG. 11 is a flowchart showing a typical procedure for step SB6 at the time of a tube current modulation irradiation mode in FIG. 8.

FIG. 11 is a flowchart showing a typical procedure for step SB6 in the tube current modulation irradiation mode. As shown in FIG. 11, first of all, the valid beat determination unit 56 checks whether the processing in step SB6.4 is to be performed on a time [ms] or phase [%] basis (step SB6.1). If, for example, a reconstruction phase is defined by a time, the processing in step SB6.4 is performed on a time basis. If a reconstruction phase is defined by a phase, the processing in step SB6.4 is performed on a phase basis.

Upon confirming in step SB6.1 that the processing is to be performed on a time basis, the valid beat determination unit 56 calculates a start phase [ms] and an end phase [ms] on a time [ms] basis. The start phase [ms] is defined by equation (1) including a high tube current irradiation start time Ths and a reconstruction time Tr. An end phase [ms] is defined by equation (2) including a high tube current irradiation end time The and a reconstruction time Tr.

$$\text{start phase[ms]} = Ths + Tr/2 \quad (1)$$

$$\text{end phase[ms]} = The - Tr/2 \quad (2)$$

Upon confirming in step SB6.1 that the processing is to be performed on a phase basis, the valid beat determination unit 56 calculates a start phase [%] and an end phase [%] on a phase [%] basis (step SB6.3). The start phase [ms] is defined by equation (3) including a high tube current irradiation start time Ths, a reconstruction time Tr, and an RR period Trr. An end phase [ms] is defined by equation (4) including a high tube current irradiation end time The, a reconstruction time Tr, and an RR period Trr.

$$\text{start phase[\%]} = ((Ths + Tr/2)/Trr) \times 100 \quad (3)$$

$$\text{end phase[\%]} = ((The - Tr/2)/Trr) \times 100 \quad (4)$$

If the processing time point of step SB6.2 comes after the input time point of the immediately preceding R trigger, the high tube current irradiation start time Ths in equations (1) and (3) is set to a positive value. If the processing time point of step SB6.2 comes before the input time point of the immediately preceding R trigger, the high tube current irradiation start time Ths in equations (1) and (3) is set to a negative value. If high tube current irradiation is not complete at the processing time point of step SB6.2, the high tube current irradiation end time The in equations (2) and (4) is set to the input time point of the latest R trigger or the scheduled end time of high tube current irradiation.

After step SB6.2 or SB6.3, the valid beat determination unit 56 determines whether X-rays have been applied with a high tube current at a reconstruction phase (step SB6.4). More specifically, the valid beat determination unit 56 determines whether an end phase is equal to or more than a reconstruction phase and a start phase is equal to or less than the reconstruction phase. If the end phase is equal to or more than the reconstruction phase and the start phase is equal to or less than the reconstruction phase, the valid beat determination unit 56 determines that X-rays have been applied with a high tube current at the reconstruction phase. If the end phase is equal to or more than the reconstruction phase and the start phase is equal to or less than the reconstruction phase, the valid beat determination unit 56 determines that X-rays have been applied with a high tube current at the reconstruction phase.

If the valid beat determination unit 56 determines in step SB6.4 that X-rays have not been applied with a high tube current at the reconstruction phase (NO in step SB6.4), the process advances to step SB7 in FIG. 10. In this case, the system control unit 54 causes the time determination unit 42 to perform determination processing (step SB7). The time determination unit 42 determines whether the scan elapsed time has exceeded the scheduled scan time or the total irradiation time has exceeded the scheduled irradiation time, as in step SA6 or SD6.

If the time determination unit 42 determines in step SB7 that the scan elapsed time has not exceeded the scheduled scan time, or the total irradiation time has not exceeded the scheduled irradiation time (NO in step SB7), the system control unit 54 returns to step SA3 in FIG. 10 to continue the scan. Note that the determination processing in step SB6 is repeatedly performed until the next R trigger is input.

If the valid beat determination unit 56 determines in step SB6.4 in FIG. 11 that X-rays have been applied with a high tube current at the reconstruction phase (YES in step SB6.4), or the time determination unit 42 determines in step SB7 in FIG. 9 that the scan elapsed time has exceeded the scheduled scan time or the total irradiation time has exceeded the scheduled irradiation time (YES in step SB7), the system control unit 54 causes the scan control unit 44 to perform termination processing (step SB8). In step SB8, the scan control unit 44 controls the rotation driving unit 18, the high voltage generation unit 22, and the data acquisition circuit 24 to terminate the scan as in step SA7.

Upon performing in step SB8, the apparatus terminates the ECG gated scanning according to the third embodiment.

As described above, if an RR period is equal to or more than the threshold T, the valid beat determination unit 56 determines, for each beat (for each RR period), in step SB6 whether a valid beat condition is satisfied. If the valid beat condition is satisfied, the corresponding beat (RR period) is confirmed as a valid beat. In this case, it is estimated that projection data which can be substantially used for the reconstruction of image data at the reconstruction phase. The apparatus therefore terminates the scan. In contrast, if the valid beat condition is not satisfied, the corresponding beat (RR period) is not valid. That is, the beat is confirmed as an invalid beat. In this case, even if the RR period of this beat is equal to or more than the threshold T, it is estimated that necessary and sufficient projection data which can be substantially used for the reconstruction of image data at the reconstruction phase have not been acquired. The apparatus therefore continues the scan. According to the third embodiment, therefore, it is possible to acquire necessary and sufficient projection data which can be substantially used for the reconstruction of image data at the reconstruction phase, more reliably than the first and second embodiments. Consequently, the X-ray CT apparatus according to the third embodiment improves the scan efficiency as compared with the X-ray CT apparatus according to the first embodiment.

As described above, the X-ray CT apparatus according to the third embodiment can improve the scan efficiency concerning ECG gated scanning.

Fourth Embodiment

An X-ray CT apparatus according to the fourth embodiment is mainly targeted at the segment reconstruction method. The X-ray CT apparatus according to the fourth embodiment counts the number of beats (the number of valid beats) satisfying a valid beat condition for the respective beats. If the number of valid beats has reached a target count or an upper limit value, the apparatus terminates the scan. The X-ray CT apparatus according to the fourth embodiment will be described below. Note that the same reference numerals in the following description denote constituent elements having almost the same functions as in the first, second, and third embodiments, and a repetitive description will be made only when required.

Figure 12:
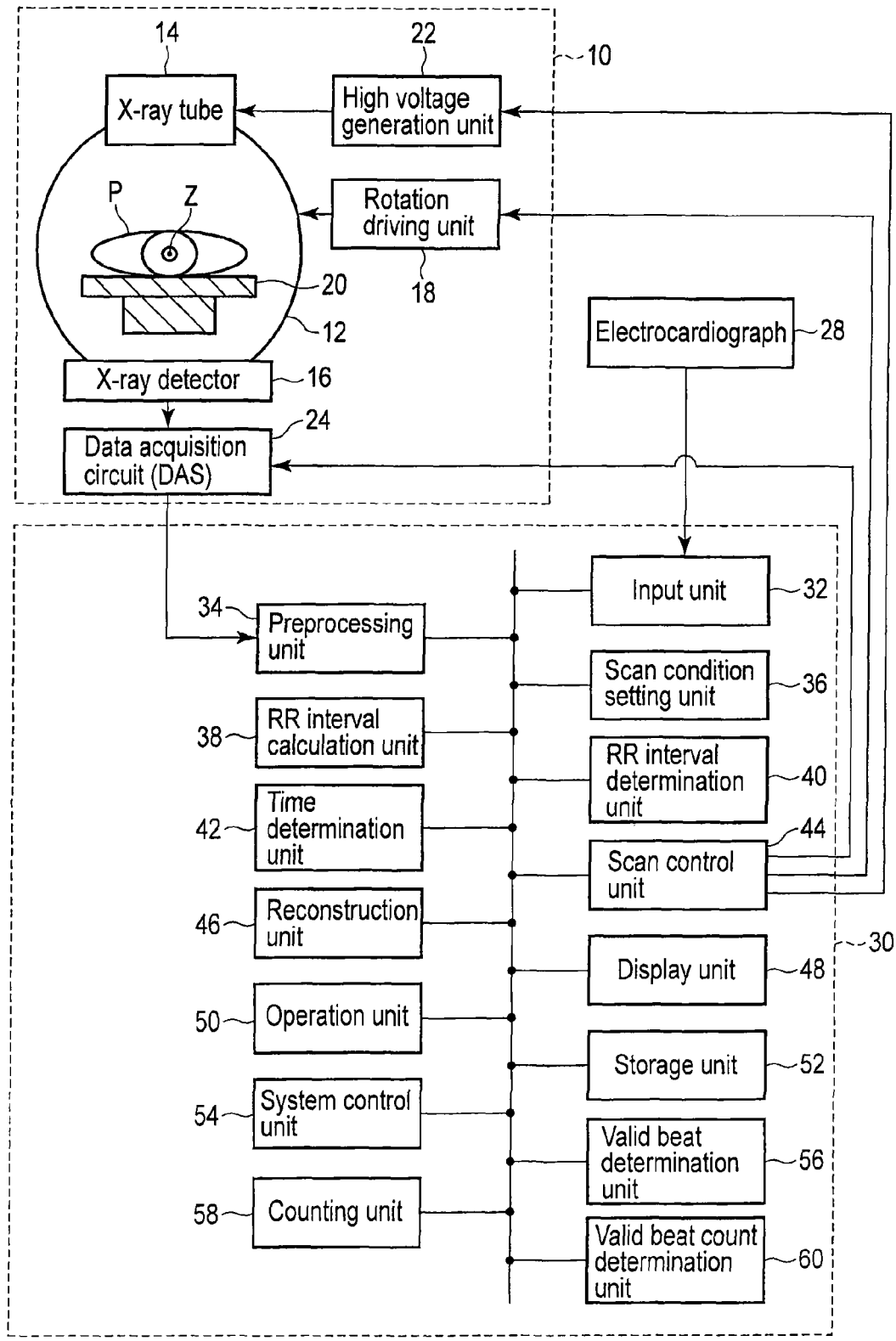
FIG. 12 is a block diagram showing the arrangement of an X-ray computed tomography apparatus according to the fourth embodiment.

FIG. 12 is a block diagram showing the arrangement of the X-ray CT apparatus according to the fourth embodiment. As shown in FIG. 12, the X-ray CT apparatus according to the fourth embodiment further includes a counting unit 58 and a valid beat count determination unit 60.

An RR period determination unit 40 compares the latest RR period with a threshold Tn to determine whether the latest RR period is equal to or more than the threshold Tn. The threshold Th is set for each segment count n concerning reconstruction processing. The threshold Tn correlates to a target count Btn of a valid beat count (to be described later). Note that the threshold Tn can be arbitrarily set in accordance with an instruction from the operator via an operation unit 50.

The counting unit 58 counts the number of beats (the number of valid beats) satisfying a valid beat condition for each segment count n. As described above, a valid beat condition is defined to whether projection data which can be substantially used for the reconstruction of image data at a reconstruction phase have been acquired.

The valid beat count determination unit 60 determines whether the valid beat count has reached the target count Btn. The target count Btn corresponds to the segment count n in the segment reconstruction method. Note that when using the half reconstruction method or the full reconstruction method, it is preferable to set the target count to 1. If, for example, the target count Btn is n, the threshold Tn is set to a time interval in which projection data necessary and sufficient for each segment can be acquired in the segment reconstruction method with the segment count n. Note that the threshold Tn may not be decided in accordance with the target count Btn. For example, the target count Btn may be decided in accordance with the threshold Tn satisfied by each RR period. Note that a scan condition setting unit 36 may set a target count in advance in accordance with an instruction from the operator via the operation unit 50. Upon determining that the valid beat count has not reached the target count, the valid beat count determination unit 60 determines whether the valid beat count has reached the upper limit value. The upper limit value is the upper limit value of a beat count in segment reconstruction.

If the valid beat count determination unit 60 determines that the valid beat count has reached the target count or that the valid beat count has not reached the target value and it is determined that the elapsed time has exceeded the scheduled scan time (or the total irradiation time has exceeded the scheduled irradiation time), a scan control unit 44 controls a high voltage generation unit 22 so as to terminate the generation of X-rays from an X-ray tube 14. If the valid beat count determination unit 60 determines that the valid beat count has not reached the target count and the beat count has not reached the upper limit value, the scan control unit 44 controls the high voltage generation unit 22 so as to continue the generation of X-rays from the X-ray tube 14. If the valid beat count determination unit 60 determines that the scan elapsed time has not exceeded the scheduled scan time (or the total irradiation time has not exceeded the scheduled irradiation time), the scan control unit 44 controls the high voltage generation unit 22 so as to continue the generation of X-rays from the X-ray tube 14.

ECG gated scanning according to the fourth embodiment will be described below.

Figure 13:
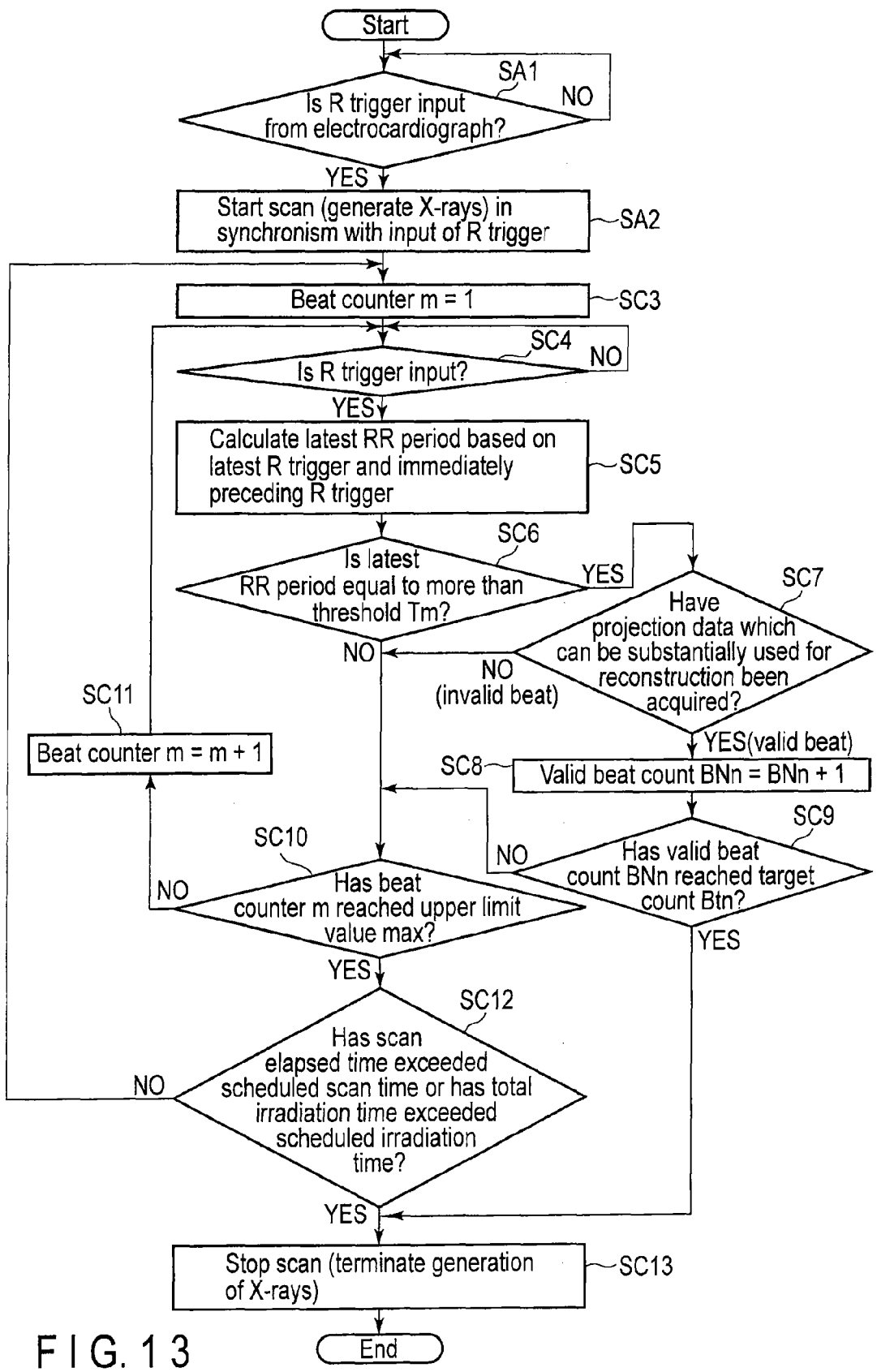
FIG. 13 is a flowchart showing a typical procedure for ECG gated scanning performed under the control of a system control unit in FIG. 12.

FIG. 13 is a flowchart showing a typical procedure for ECG gated scanning performed under the control of the system control unit 54 according to the fourth embodiment. The same reference numerals denote steps of the same processing contents as those in ECG gated scanning in FIGS. 3 and 6, and a description of them will be omitted.

Upon starting a scan in step SA2, the system control unit 54 causes the counting unit 58 to perform setting processing (step SC3). In step SC3, the counting unit 58 sets a beat counter m to an initial value (e.g., 1). The beat counter m indicates a set beat count.

Upon performing step SC3, the system control unit 54 waits for the input of an R trigger from an electrocardiograph 28 via an input unit 32 (step SC4).

When an R trigger is input in step SC4, the system control unit 54 causes the RR period calculation unit 38 to perform calculation processing (step SC5). In step SC5, the RR period calculation unit 38 calculates the latest RR period based on the input time point of the latest R trigger and the input time point of the immediately preceding R trigger.

Upon performing step SC5, the system control unit 54 causes the RR period determination unit 40 to perform determination processing (step SC6). In step SC6, the RR period determination unit 40 compares the latest RR period with the threshold Tn to determine, for each threshold Tn, whether the latest RR period is equal to or more than the threshold Tn. Note that n=1 to m.

If the RR period determination unit 40 determines in step SC6 that the latest RR period is not equal to or more than the threshold Tn (NO in step SC6), the system control unit 54 causes the valid beat determination unit 56 to perform determination processing (step SC7). In step SC7, the valid beat determination unit 56 determines, by the same method as in step SB6, whether the valid beat condition corresponding to the X-ray irradiation mode is satisfied. If the valid beat determination unit 56 determines that the valid beat condition is satisfied, the system control unit 54 confirms the latest beat (latest RR period) as a valid beat. If the valid beat determination unit 56 determines that the valid beat condition is not satisfied, the system control unit 54 confirms the latest beat (latest RR period) as an invalid beat.

If the valid beat determination unit 56 determines in step SC7 that the valid beat condition is satisfied (YES in step SC7), the system control unit 54 causes the counting unit 58 to perform counting processing (step SC8). In step SC8, the counting unit 58 increments a valid beat count BNn by 1 (BNn=BNn+1). Note that at the start of ECG gated scanning, the valid beat count BNn is set to 0.

Upon performing step SC8, the system control unit 54 causes the valid beat count determination unit 60 to perform the first determination processing (step SC9). In step SC9, the valid beat count determination unit 60 determines whether the valid beat count BNn has reached the target count Btn for each n.

If the valid beat count determination unit 60 determines that the valid beat count BNn has not reached the target count Btn (NO in step SC9), the system control unit 54 causes the valid beat count determination unit 60 to perform the second determination processing (step SC10). In step SC10, the valid beat count determination unit 60 determines that the beat counter m has reached an upper limit value max.

If the valid beat count determination unit 60 determines in step SC10 that the beat counter m has not reached the upper limit value max (NO in step SC10), the system control unit 54 causes the counting unit 58 to perform incremental processing (step SC11). In step SC11, the counting unit 58 increments the beat counter m by 1.

Upon performing step SC11, the system control unit 54 advances to step SC4. The system control unit 54 then repeats steps SC4 to SC10 until the valid beat count determination unit 60 determines in step SC9 that the valid beat count BNn has reached the target count Btn or determines in step SC10 that the beat counter m has reached the upper limit value max.

If the valid beat count determination unit 60 determines in step SC10 that the beat counter m has reached the upper limit value max (YES in step SC10), the system control unit 54 causes a time determination unit 42 to perform determination processing (step SC12). In step SC12, the time determination unit 42 determines, by the same method as in step SA6 or SD6, whether the scan elapsed time has exceeded the scheduled scan time or the total irradiation time has exceeded the scheduled irradiation time.

If the time determination unit 42 determines in step SC12 that the scan elapsed time has exceeded the scheduled scan time or the total irradiation time has exceeded the scheduled irradiation time (NO in step SC12), the system control unit 54 advances to step SC3. The system control unit 54 repeats steps SC4 to SC12 until the valid beat count determination unit 60 determines in step SC9 that the valid beat count BNn has reached the target count Btn or the time determination unit 42 determines in step SC12 that the scan elapsed time has exceeded the scheduled scan time (or the total irradiation time has exceeded the scheduled irradiation time).

If the valid beat count determination unit 60 determines in step SC9 that the valid beat count BNn has reached the target count Btn (YES in step SC9) or the time determination unit 42 determines in step SC12 that the elapsed time has exceeded the scheduled scan time (or the total irradiation time has exceeded the scheduled irradiation time) (YES in step SC12), the system control unit 54 causes the scan control unit 44 to perform termination processing (step SC13). In step S13, the scan control unit 44 controls the rotation driving unit 18, the high voltage generation unit 22, and the data acquisition circuit 24 to terminate the scan by the same method as in step SA7 or SB8.

Upon performing step SC13, the apparatus terminates the ECG gated scanning according to the fourth embodiment.

As described above, in step SC7, the valid beat determination unit 56 determines, for each segment count n, whether a valid beat condition is satisfied for each beat (each RR period). If the valid beat condition is satisfied, the corresponding beat is confirmed as a valid beat. In step SC8, the counting unit 58 increments the valid beat count BNn by 1. If the valid beat condition is not satisfied, the corresponding beat is confirmed as not a valid beat. If the valid beat condition is satisfied, the valid beat count determination unit 60 determines, for each segment count n, in step SC9 whether the valid beat count BNn has reached the target count Btn. If the valid beat count BNn has reached the target count Btn, it indicates that projection data necessary and sufficient for segment reconstruction have been acquired. In this case, therefore, the scan control unit 44 terminates the scan in step SC13. If the valid beat count BNn has not reached the target count Btn, it indicates that projection data which can be substantially used for segment reconstruction have been acquired. In this case, therefore, the apparatus continues the scan. Even if, however, the valid beat count BNn has not reached the target count Btn, the apparatus terminates the scan to prevent a subject P from being excessively exposed to X-rays, if the beat count has reached the upper limit value and the elapsed time has reached the scheduled scan time (or the total irradiation time has reached the scheduled irradiation time).

Upon completion of the ECG gated scanning, a reconstruction unit 46 performs segment reconstruction processing for the acquired projection data to generate image data. The projection data used for reconstruction is the projection data acquired at a valid beat. The reconstruction unit 45 automatically selects projection data to be used based on, for example, the status information of the projection data.

Figures 14, 15:
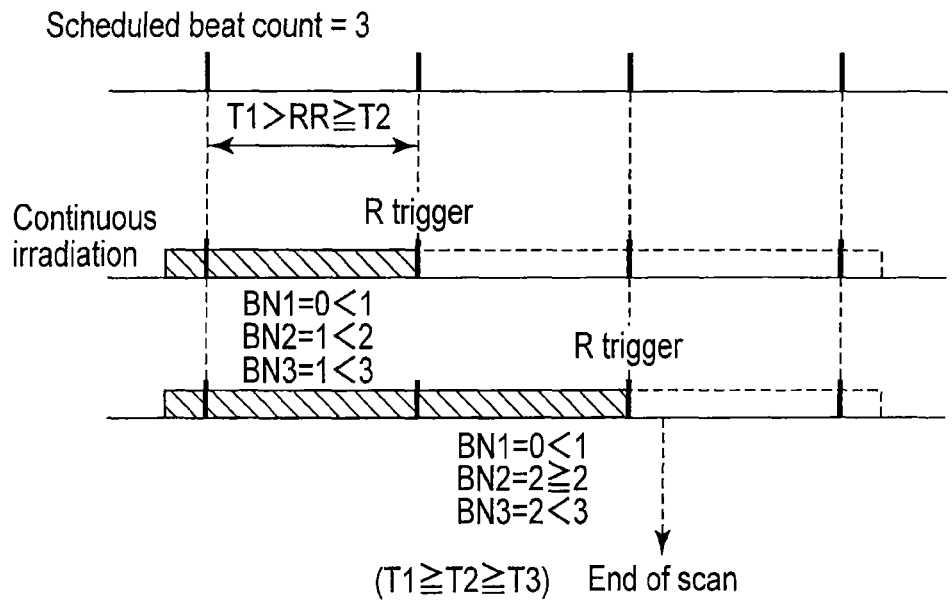
FIG. 14 is a view schematically showing ECG gated scanning according to the fourth embodiment.
FIG. 15 is a view for explaining the status information of projection data used by a reconstruction unit in FIG. 12.

Reconstruction using status information will be concretely described below with reference to FIGS. 14 and 15. FIG. 14 is a chart schematically showing ECG gated scanning according to the third embodiment. Assume that FIG. 14 shows the continuous irradiation mode, and the scheduled beat count is 3. Note that threshold T1≥threshold T2≥threshold Th3. Assume that at the first beat, the RR period is smaller than the threshold T1 and larger than the threshold T2. At the first beat, therefore, the valid beat condition concerning half reconstruction is not satisfied, the valid beat condition concerning the segment count "2" is satisfied, and the valid beat condition concerning the segment count "3" is satisfied. In this case, BN1=0, BN2=1, and BN3=1. At the first beat, BN=0<1, BN2=1<2, and BN3=1<3, and hence the apparatus continues the scan. Assume that at the second beat, the RR period is smaller than the threshold T1 and larger than the threshold T2. At the second beat, therefore, the valid beat condition concerning half reconstruction is not satisfied, the valid beat condition concerning the segment number "2" is satisfied, and the valid beat condition concerning the segment number "3" is satisfied. In this case, BN1=0, BN2=2, and BN3=2. At the second beat, BN=0<1, BN2=2≥2, and BN3=2<3, and hence the valid beat condition concerning the segment count "2" is satisfied. Therefore, the apparatus terminates the scan before the imaging beat count reaches the scheduled beat count "3".

FIG. 15 is a view showing an example of the status information of projection data. Status information includes a beat number and information indicating whether the corresponding beat is a valid beat. A storage unit 52 stores acquired data while associating beat numbers with information indicating whether each beat is a valid beat. The reconstruction unit 45 selects projection data, of the projection data stored in the storage unit 52, which are associated with information indicating that the corresponding beats are valid beats. In the case shown in FIG. 14, the reconstruction unit 45 selects the projection data at the first beat and the projection data at the second beat. If, for example, the second beat is an invalid beat, it is preferable to select the projection data at the first beat and the projection data at the third beat. The reconstruction unit 45 reads out the selected projection data from the storage unit 52 and reconstructs image data based on the readout projection data. Since projection data used for reconstruction are automatically selected in this manner, the X-ray CT apparatus according to the third embodiment can shorten the operation time of the operator at the time of reconstruction.

In the above description, the scan condition setting unit 36 may decide the threshold Tn in accordance with the target count Btn of a valid beat count and a scan condition. In this case, scan conditions include the rotational speed of a rotating frame 12, a reconstruction method, and a scan target. The scan target includes, for example, the disease condition of the heart of the subject P, e.g., information indicating whether the heart has arrhythmia.

FIG. 16 is a view showing an example of a table which outputs the threshold Tn upon receiving the target count Btn of a valid beat count and a scan condition. For example, if the target count Btn is 1 with scan condition 1, the scan condition setting unit 36 inputs scan condition 1 and the target count Btn to the above table. The above table outputs threshold T1=1100 ms associated with scan condition 1 and the target count Btn. The scan condition setting unit 36 sets the threshold T1 to 1100 ms. Deciding the threshold Tn by using the table in accordance with the target count Btn and the scan condition makes it easy to decide the threshold Tn, thereby reducing the load on the operator at the time of scan planning.

As described above, the X-ray CT apparatus according to the third embodiment can improve the scan efficiency concerning ECG gated scanning.

(First Modification)

In the third and fourth embodiments, if the RR period determination unit 40 determines that the threshold T or Tn is larger than the latest RR period, the valid beat determination unit 56 determines whether projection data which can be substantially used for reconstruction have been acquired. However, this embodiment is not limited to this. For example, every time the latest R trigger is input, the valid beat determination unit 56 may determine whether projection data which can be substantially used for reconstruction have been acquired, instead of performing determination by the RR period determination unit 40. If the valid beat determination unit 56 determines that projection data which can be substantially used for reconstruction have not been acquired, the scan control unit 44 controls the high voltage generation unit 22 to continue the generation of X-rays from the X-ray tube 14. If the valid beat determination unit 56 determines that projection data which can be substantially used for reconstruction have been acquired, the scan control unit 44 controls the high voltage generation unit 22 to terminate the generation of X-rays from the X-ray tube 14.

As described above, the X-ray CT apparatus according to the first modification can improve the scan efficiency concerning ECG gated scanning.

(Second Modification)

In the above embodiments, the determination target of the time determination unit 42 is a scan elapsed time or a total irradiation time. However, the determination target of the time determination unit 42 may be combination of a scan elapsed time and a total irradiation time. In this case, the procedure for ECG gated scanning in FIG. 3 (or FIG. 6) incorporates the determination processing of determining whether the scan elapsed time has exceeded the scheduled scan time (step SA6) and the determination processing of determining whether the total irradiation time has exceeded the scheduled irradiation time (step SD6). The order of execution of steps SA6 and SD6 is not specifically limited. For example, if it is determined that the total irradiation time has not exceeded the scheduled irradiation time, it is preferable to determine whether the scan elapsed time has exceeded the scheduled scan time. That is, if one of the scan elapsed time and the total irradiation time has exceeded a scheduled time, the apparatus terminates the scan to reduce radiation dosage.

As described above, the X-ray CT apparatus according to the second modification can improve the scan efficiency concerning ECG gated scanning.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus comprising:
an X-ray tube configured to generate X-rays;
an X-ray detector configured to detect X-rays generated from the X-ray tube and transmitted through a subject;
a support mechanism configured to rotatably support the X-ray tube and the X-ray detector;
an input unit configured to repeatedly input, from an electrocardiograph, a trigger signal originating from a specific cardiac phase in a cardiac cycle of the heart of the subject;
an RR period determination unit configured to determine whether a period between an input time point of a latest trigger signal, of the repeatedly input trigger signals, and an input time point of a trigger signal immediately before the latest trigger signal is not less than a preset first threshold, for each input of the latest trigger signal;
a condition determination unit configured to determine whether projection data which is configured to be substantially used for image reconstruction at a reconstruction target phase have been acquired, if it is determined that the period is not less than the first threshold;
a control unit configured to terminate generation of X-rays from the X-ray tube, if it is determined that the projection data which is configured to be substantially used have been acquired.

2. The X-ray computed tomography apparatus of claim 1, further comprising an elapsed time determination unit configured to determine whether an elapsed time from a start time point of a scan has exceeded a second threshold indicating a preset scheduled scan time,
wherein the condition determination unit is configured to determine whether projection data which is configured to be substantially used for image reconstruction at a reconstruction target phase have been acquired, if it is determined that the period is not less than the first threshold or the elapsed time has exceeded the second threshold, and
the control unit terminates generation of X-rays from the X-ray tube, if it is determined that the projection data which is configured to be substantially used have been acquired.

3. The X-ray computed tomography apparatus of claim 1, further comprising an elapsed time determination unit configured to determine whether an elapsed time from a start time point of a scan has exceeded a second threshold indicating a preset scheduled scan time,
wherein the elapsed time determination unit determines whether the elapsed time has exceeded the second threshold, if it is determined that the period is less than the first threshold, and
the control unit terminates generation of X-rays from the X-ray tube, if it is determined that the projection data which is configured to be substantially used have been acquired or it is determined that the elapsed time has exceeded the second threshold.

4. The X-ray computed tomography apparatus of claim 1, further comprising a tube current control unit configured to control a tube current flowing in the X-ray tube so as to alternately switch between a first current value and a second current value smaller than the first current value,
wherein the condition determination unit determines whether the reconstruction target phase is included in a first period in which the tube current has the first current value, if it is determined that the period is not less than the first threshold, and
the control unit terminates generation of X-rays from the X-ray tube, if it is determined that the reconstruction target phase is included in the first period.

5. The X-ray computed tomography apparatus of claim 3, further comprising a tube current control unit configured to control a tube current so as to alternately generate the X-rays and stop generating the X-rays,
wherein the condition determination unit determines whether the reconstruction target phase is included in an irradiation period in which the X-rays are generated, if it is determined that the period is not less than the first threshold, and
the control unit terminates generation of the X-rays, if it is determined that the reconstruction target phase is included in the irradiation period.

6. The X-ray computed tomography apparatus of claim 3, further comprising:
a counting unit configured to count a beat count when it is determined that the projection data which is configured to be substantially used have been acquired; and
a valid count determination unit configured to determine whether the beat count has reached a preset target count, wherein the elapsed time determination unit determines whether the elapsed time has exceeded the second threshold, if it is determined that the beat count has not reached the target count, and the control unit terminates generation of the X-rays from the X-ray tube, if it is determined that the beat count has reached the target count or it is determined that the beat count has not reached the target count and it is determined that the elapsed time has exceeded the second threshold.

7. The X-ray computed tomography apparatus of claim 2, wherein the second threshold is set in accordance with an instruction from a user.

8. The X-ray computed tomography apparatus of claim 1, further comprising an irradiation time determination unit configured to determine whether a total irradiation time of X-rays from the X-ray tube has exceeded a second threshold indicating a preset scheduled irradiation time, wherein the control unit terminates generation of X-rays from the X-ray tube, if it is determined that the projection data which is configured to be substantially used have been acquired or it is determined that the total irradiation time has exceeded the second threshold.

9. The X-ray computed tomography apparatus of claim 1, wherein the first threshold is set based on a period of one pulsation of the subject which is measured in advance.

10. The X-ray computed tomography apparatus of claim 2, further comprising a tube current control unit configured to control a tube current so as to alternately generate the X-rays and stop generating the X-rays, wherein the condition determination unit determines whether the reconstruction target phase is included in an irradiation period in which the X-rays are generated, if it is determined that the period is not less than the first threshold, and the control unit terminates generation of the X-rays, if it is determined that the reconstruction target phase is included in the irradiation period.

11. The X-ray computed tomography apparatus of claim 3, wherein the second threshold is set in accordance with an instruction from a user.

* * * * *